United States Patent
Gaul et al.

(10) Patent No.: US 7,622,579 B2
(45) Date of Patent: Nov. 24, 2009

(54) HETERO ISONIPECOTIC MODULATORS OF VANILLOID VR1 RECEPTOR

(75) Inventors: Micheal D. Gaul, Yardley, PA (US); Bao-Ping Zhao, West Windsor, NJ (US); Daniel A. Hutta, Belle Mead, NJ (US)

(73) Assignee: Janssen Pharmaceutica NV (BE)

( * ) Notice: Subject to any disclaimer, the term of this patent is extended or adjusted under 35 U.S.C. 154(b) by 480 days.

(21) Appl. No.: 11/168,213

(22) Filed: Jun. 27, 2005

(65) Prior Publication Data

US 2005/0288281 A1    Dec. 29, 2005

Related U.S. Application Data

(60) Provisional application No. 60/583,326, filed on Jun. 28, 2004.

(51) Int. Cl.
*C07D 417/02*     (2006.01)
*C07D 279/12*     (2006.01)
(52) U.S. Cl. ................................. 544/63; 514/227.8
(58) Field of Classification Search .............. 514/227.8; 544/63
See application file for complete search history.

(56) References Cited

FOREIGN PATENT DOCUMENTS

| WO | WO 96/10022 | 4/1996 |
|----|-------------|--------|
| WO | WO 97/06802 | 2/1997 |
| WO | WO 98/06705 | 2/1998 |
| WO | WO 03/068749 | 8/2003 |
| WO | WO 03/103669 | 12/2003 |
| WO | WO 2004/035549 | 4/2004 |
| WO | WO 2004/101546 | 11/2004 |

OTHER PUBLICATIONS

Chemcats 2032356618 , RN 909501-10-6 (2007).*
Lee et al. "anlysis of structure . . . " Bioorg. Med. chem. v. 12, p. 3411-3420 (2004).*
Suh et al. "Nobel non-vanilloid . . . " Bioorg. Med. Chem. Lett. v.13, p. 4389-4393 (2003).*
Szallasi et al. "Vanilloid receptor . . . " J. Med. Chem. v. 47 (11) p. 2717-2723 (2004).*
Brown, G.R. et al., "A Novel Series of 4-Piperidinopyridine and 4-Piperidinopyrimidine inhibitors of 2,3-Oxidosqualene Cyclase-Lanosterol Synthase", Journal of Medicinal Chemistry, vol. 43, No. 26, 2000, pp. 4964-4972.
Brown, G.R. et al., "Novel 4-Piperidinopyridine Inhibitors of Oxidosqualene Cyclase-Lanosterol Synthase Derived by Consideration of Inhibitor pKa", Bioorganic & Medicinal Chemistry Letters, vol. 11, 2001, pp. 2213-2216.
Walpole, C.S.J. et al., "The discovery of Capsazepine, the first competitive antagonist of the sensory neuron excitants capsaicin and resiniferatoxin", Journal of Medicinal chemistry, American Chemical Society, Washington, US, vol. 37, 1994, pp. 1942-1954.
Brown, G.R. et al., "A Novel Series of 4-Piperidinopyridine and 4-Piperidinopyrimidine inhibitors of 2,3-Oxidosqualene Cyclase-Lanosterol Synthase", Journal of Medicinal Chemistry, vol. 43, No. 26, 2000, pp. 4964-4972.

* cited by examiner

*Primary Examiner*—Celia Chang

(57) ABSTRACT

This invention is directed to vanilloid receptor VR1 ligands. More particularly, this invention relates to hetero isonipecotic amides that are potent modulators of VR1 which are useful for the treatment and prevention of disease conditions in mammals.

14 Claims, No Drawings

HETERO ISONIPECOTIC MODULATORS OF VANILLOID VR1 RECEPTOR

This application claims priority to U.S. Provisional Patent Application No. 60/583,326 filed on Jun. 28, 2004. The complete disclosures of the aforementioned related U.S. patent application is hereby incorporated herein by reference for all purposes.

CROSS-REFERENCE TO RELATED APPLICATIONS

This application claims priority to U.S. Provisional Application No. 60/583,326, filed Jun. 28, 2004.

STATEMENT REGARDING FEDERALLY SPONSORED RESEARCH OR DEVELOPMENT

The research and development of the invention described below was not federally sponsored.

BACKGROUND OF THE INVENTION

This invention is directed to novel vanilloid receptor VR1 ligands. More particularly, this invention relates to novel hetero isonipecotic amides that are potent modulators of VR1.

Noxious chemical, thermal and mechanical stimuli excite peripheral nerve endings of small diameter sensory neurons (nociceptors) in sensory ganglia (e. g., dorsal root, nodose and trigeminal ganglia) and initiate signals that are perceived as pain. These neurons are crucial for the detection of harmful or potentially harmful stimuli (heat) and tissue damage (local tissue acidosis and/or stretch) that arise from changes in the extracellular space during inflammatory or ischaemic conditions (Wall, P. D., and Melzack, R., *Textbook of Pain*, 1994, New York: Churchill Livingstone). Nociceptors transduce noxious stimuli into membrane depolarization that triggers action potential, conducts the action potential from the sensory sites to the synapses in the CNS, and conversion of action potentials invokes a perception of pain, discomfort, and appropriate mechanical/physical protective reflexes. At the molecular level, nociception is carried out by ion channels or receptors. Plant derived vanilloid compounds (capsaicin and its ultrapotent analog, resiniferatoxin, etc.) are known to selectively depolarize nociceptors and elicit sensations of burning pain—the sensation that is typically obtained by hot chili peppers. Therefore, capsaicin mimics the action of physiological/endogenous stimuli that activates the "nociceptive pathway". Recent advances in pain biology have identified receptors for vanilloids, protons (i.e., acidic solutions), and for heat. Because nociceptors are involved with unwanted pain and inflammatory conditions in human beings and animals, modulation of their nociceptive pathway is important in palliative and other therapies.

Walpole and colleagues at Sandoz reported on the first competitive antagonist of the sensory neuron excitants capsaicin and resineriferatoxin (Walpole, C. S. J. et. al., *J. Med. Chem.* 1994, 37, 1942). Subsequently, capsazepine has been shown to be a vanilloid receptor antagonist.

SUMMARY OF THE INVENTION

The invention is directed to compounds of formula (I)

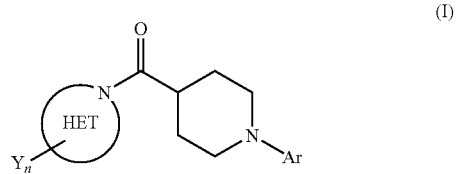

wherein

is a 4 to 8 membered cyclic heteroalkyl group bonded to the rest of the molecule through a ring nitrogen atom and optionally containing 1-2 heteroatoms in addition to said ring nitrogen atom, wherein the optional 1-2 additional heteroatoms are independently selected from the group consisting of N, O and S; or a 5 to 10 membered heteroaryl group bonded to the rest of the molecule through a ring nitrogen atom and selected from the group consisting of dihydroquinoline, tetrahydroquinoline, dihydroisoquinoline, tetrahydroisoquinoline, benzimidazole, imidazole, imidazoline, indazole, indole, indoline, isoindole, isoindoline, pyrazole, pyrrole, and triazole;

Y is bonded to

at a substitutable atom and is independently selected from the group consisting of hydrogen; hydroxyl; $R^1$; $R^1O$—; $R^1S$—; $CF_3O$—; $R^1S(O)$—; $R^1SO_2$—; -LCOX; $C_{6-10}$aryl; a 3 to 7 membered cyclic heteroalkanyl containing from 1 to 3 heteroatoms wherein said heteroatoms independently are N, O or S; and a 5 to 10 membered heteroaryl selected from the group consisting of benzofuran, benzimidazole, benzisoxazole, benzthiazole, benzothiophene, benzoxazole, cinnoline, furan, imidazole, imidazoline, indazole, indole, indoline, indolizine, isobenzofuran, isoindole, isoindoline, isoquinoline, isothiazole, isoxazole, naphthyridine, oxadiazole, oxazole, pthalazine, pteridine, purine, pyran, pyrazine, pyrazole, pyridazine, pyridine, pyrimidine, pyrrole, pyrrolizine, quinoline, quinolizine, quinazoline, quinoxaline, tetrazole, thiadiazole, thiazole, thiophene, triazine, and triazole;

n is an integer from 0 to 4;

Ar is phenyl; naphthyl; a 5-6 membered heteroaryl ring selected from the group consisting of furan, imidazole, isothiazole, isoxazole, oxadiazole, oxazole, pyran, pyrazine, pyrazole, pyridazine, pyrrole, tetrazole, thiadiazole, triazine, and triazole; or a fused 5,6 or 6,6 heteroaryl selected from the group consisting of benzimidazole, benzisoxazole, benzofuran, benzoxazole, benzthiazole, benzothiophene, cinnoline, indazole, indole, indoline, indolizine, isobenzofuran, isoindole, isoindoline, isoquinoline, naphthyridine, pthalazine, pteridine, pyrrolizine, quinoline, and quinolizine; wherein Ar is optionally substituted with one to four substituents independently selected from the group consisting of halogen; $R^1$; fluorinated $C_{1-10}$alkyl; phenyl; amino; cyano; $CF_3O$—; a 3 membered cyclic heteroalkyl containing 1 heteroatom that is N, O or S wherein said 3 membered cyclic heteroalkyl is optionally substituted with a substituent that is halogen, $R^1$, fluorinated $C_{1-10}$ alkyl, amino, cyano, $CF_3O$—, $R^1O$—, $R^1S$—, $R^1SO_2$—, $R^1S(O)$—, $R^1SO_2NH$—, or -LCOX; a 4 to 5 membered cyclic heteroalkyl containing 1-3 heteroatoms that independently are N, O or S wherein said 4 to 5 membered cyclic heteroalkyl is optionally substituted with 1 to 2 substituents that independently are halogen, $R^1$, fluorinated $C_{1-10}$alkyl, amino, cyano, $CF_3O$—, $R^1O$—, $R^1S$—, $R^1SO_2$—, $R^1S(O)$—, $R^1SO_2NH$—, or -LCOX; a 6 to 7 membered cyclic heteroalkyl containing 1-3 heteroatoms that independently are N, O or S wherein said 6 to 7 membered cyclic heteroalkyl is optionally substituted with 1 to 3 substituents that independently are halogen, $R^1$, fluorinated $C_{1-10}$alkyl, amino, cyano, $CF_3O$—, $R^1O$—, $R^1S$—, $R^1SO_2$—, $R^1S(O)$—, $R^1SO_2NH$—, or -LCOX; a heteroaryl wherein said heteroaryl is cinnoline, furan, imidazole, indazole, indole, indoline, indolizine, isobenzofuran, isoindole, isoindoline, isoquinoline, isothiazole, isoxazole, naphthyridine, oxadiazole, oxazole, pthalazine, pteridine, pyran, pyrazine, pyrazole, pyridazine, pyridine, pyrimidine, pyrrole, pyrrolizine, quinoline, quinolizine, quinazoline, quinoxaline, tetrazole, thiadiazole, triazine, or triazole wherein said heteroaryl is optionally substituted with 1 to 3 substituents that independently are halogen, $R^1$, fluorinated $C_{1-10}$alkyl, amino, cyano, $CF_3O$—, $R^1O$—, $R^1S$—, $R^1SO_2$—, $R^1S(O)$—, $R^1SO_2NH$—, or -LCOX; hydroxyl; $R^1O$—; $R^1S$—; $R^1SO_2$—; $R^1S(O)$—; $R^1SO_2NH$—; -LCOX; and $C_{6-10}$aryl;

$R^1$ is $C_{1-10}$alkyl;

L is —NH—, a direct bond, —O—, or —$CH_2$—;

X is H, $R^1$, HO, $R^1O$—, $R^1S$—, —$NH_2$, $R^1NH$—, or $(R^1)_2N$—; and enantiomers, diastereomers, tautomers, solvates, and pharmaceutically acceptable salts thereof.

DETAILED DESCRIPTION OF THE INVENTION

As used herein, the following underlined terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms.

"Fluorinated alkyl" refers to a saturated branched or straight chain hydrocarbon radical derived by removal of 1 hydrogen atom from the parent alkane; the parent alkane contains from 1 to 6 carbon atoms with 1 or more hydrogen atoms substituted with fluorine atoms up to and including substitution of all hydrogen atoms with fluorine. Preferred fluorinated alkyls include trifluoromethyl substituted alkyls and perfluorinated alkyls; more preferred fluorinated alkyls include trifluoromethyl, perfluoroethyl, 2,2,2-trifluoroethyl, perfluoropropyl, 3,3,3-trifluoroprop-1-yl, 3,3,3-trifluoroprop-2-yl, 1,1,1,3,3,3-hexafluoroprop-2-yl; a particularly preferred fluorinated alkyl is trifluoromethyl.

"Fluorinated alkanyloxy" refers to a radical derived from a fluorinated alkyl radical attached to an oxygen atom with the oxygen atom having one open valence for attachment to a parent structure.

"Alkyl:" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl , cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl", "alkenyl" and/or "alkynyl" is used, as defined below. In preferred embodiments, the alkyl groups are ($C_{1-8}$) alkyl, with ($C_{1-3}$) being particularly preferred.]

"Alkanyl:" refers to a saturated branched, straight-chain or cyclic monovalent hydrocarbon radical derived by the removal of one hydrogen atom from a single carbon atom of a parent alkane. Typical alkanyl groups include, but are not limited to, methanyl; ethanyl; propanyls such as propan-1-yl, propan-2-yl, cyclopropan-1-yl, etc.; butyanyls such as butan-1-yl, butan-2-yl, 2-methyl-propan-1-yl, 2-methyl-propan-2-yl, cyclobutan-1-yl, etc.; and the like. In preferred embodiments, the alkanyl groups are ($C_{1-8}$) alkanyl, with ($C_{1-3}$) being particularly preferred.

"Alkenyl:" refers to an unsaturated branched, straight-chain or cyclic monovalent hydrocarbon radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is ($C_{2-8}$) alkenyl, with ($C_{2-3}$) being particularly preferred.

"Alkynyl:" refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is ($C_{2-8}$) alkynyl, with ($C_{2-3}$) being particularly preferred.

"Alkyldiyl:" refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methylprop-2-en-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkandiyl, alkendiyl and/or alkyndiyl is used. In preferred embodiments, the alkyldiyl group is $(C_{1-8})$ alkyldiyl, with $(C_{1-8})$ being particularly preferred. Also preferred are saturated acyclic alkandiyl radicals in which the radical centers are at the terminal carbons, e.g., methandiyl; ethan-1,2-diyl; propan-1,3-diyl; butan-1,4-diyl; and the like (also referred to as alkylenos, as defined infra).

"Vic Alkyldiyl:" refers to a saturated or unsaturated, branched, straight-chain or cyclic hydrocarbon radical having two adjacent monovalent radical centers derived by the removal of one hydrogen atom from each of two adjacent carbon atoms of a parent alkane, alkene or alkyne. The two monovalent radical centers can form bonds with the same or different atom(s). Typical vic alkyldiyls include, but are not limited to vic ethyldiyls such as ethan-1,2-diyl, ethen-1,2-diyl; vic propyldiyls such as propan-1,2-diyl, cyclopropan-1,2-diyl, prop-1-en-1,2-diyl, prop-2-en-1,2-diyl, cycloprop-1-en-1,2-diyl, etc.; vic butyldiyls such as butan-1,2-diyl, 2-methyl-propan-1,2-diyl, cyclobutan-1,2-diyl, but-1-en-1,2-diyl, cyclobut-1-en-1,2-diyl, buta-1,3-dien-1,2-diyl, cyclobuta-1,3-dien-1,2-diyl, but-3-yn-1,2-diyl, etc.; and the like. Where specific levels of saturation are intended, the nomenclature vic alkandiyl, vic alkendiyl and/or vic alkyndiyl is used. In preferred embodiments, the vic alkyldiyl group is $(C_{2-8})$ vic alkyldiyl, with $(C_{2-3})$ being particularly preferred.

"Gem Alkyldiyl:" refers to a saturated or unsaturated, branched, straight-chain or cyclic hydrocarbon radical having one divalent radical center derived by the removal of two hydrogen atoms from a single carbon atom of a parent alkane, alkene or alkyne. The divalent radical center forms bonds with two different atoms. Typical gem alkyldiyls include, but are not limited to gem methanyidiyl; gem ethyldiyls such as ethan-1,1-diyl, ethen-1,1-diyl; gem propyldiyls such as propan-1,1-diyl, propan-2,2-diyl, cyclopropan-1,1-diyl, prop-1-en-1,1-diyl, cycloprop-2-en-1,1-diyl, prop-2-yn-1,1-diyl, etc.; butyldiyls such as butan-1,1-diyl, butan-2,2-diyl, 2-methyl-propan-1,2-diyl, cyclobutan-1,1-diyl, but-1-en-1,1-diyl, 2-methyl-prop-1-en-1,1-diyl, 2-methyl-prop-2-en-1,1-diyl, cyclobut-2-en-1,1-diyl, buta-1,3-dien-1,1-diyl, etc.; and the like. Where specific levels of saturation are intended, the nomenclature gem alkandiyl, gem alkendiyl and/or gem alkyndiyl is used. In preferred embodiments, the gem alkyldiyl group is $(C_{1-6})$ gem alkyldiyl, with $(C_{1-3})$ being particularly preferred.

"Alkyleno:" refers to a saturated or unsaturated, straight-chain or branched acyclic bivalent hydrocarbon bridge radical derived by the removal of one hydrogen atom from each of the two terminal carbon atoms of an acyclic parent alkane, alkene or alkyne. Typical alkyleno groups include, but are not limited to, methano; ethylenos such as ethano, etheno, ethyno; propylenos such as propano, propeno, prop-1,2-dieno, propyno, etc.; butylenos such as butano, 2-methyl-propano, but-1-eno, but-2-eno, 2-methyl-prop-1-eno, 2-methanylidene-propano, but-1,3-dieno, but-1-yno, but-2-yno, but-1,3-diyno, etc.; and the like. Where specific levels of saturation are intended, the nomenclature alkano, alkeno and/or alkyno is used. In preferred embodiments, the alkyleno group is $(C_{1-8})$ alkyleno, with $(C_{1-3})$ being particularly preferred. Also preferred are straight-chain saturated alkano radicals, e.g., methano, ethano, propano, butano, and the like.

"Alkylidene:" refers to a saturated or unsaturated, branched, straight-chain or cyclic divalent hydrocarbon radical derived by removal of two hydrogen atoms from the same carbon atom of a parent alkane, alkene or alkyne. The divalent radical center forms a double bond with a single atom. Typical alkylidene radicals include, but are not limited to, methanylidene, ethylidenes such as ethanylidene, ethenylidene; propylidenes such as propan-1-ylidene, propan-2-ylidene, cyclopropan-1-ylidene, prop-1-en-1-ylidene, prop-2-en-1-ylidene, cycloprop-2-en-1-ylidene, etc.; butylidenes such as butan-1-ylidene, butan-2-ylidene, 2-methyl-propan-1-ylidene, cyclobutan-1-ylidene, but-1-en-1-ylidene, but-2-en-1-ylidene, but-3-en-1-ylidene, buta-1,3-dien-1-ylidene; cyclobut-2-en-1-ylidene, etc.; and the like. Where specific levels of saturation are intended, the nomenclature alkanylidene, alkenylidene and/or alkynylidene is used. In preferred embodiments, the alkylidene group is $(C_{1-8})$ alkylidene, with $(C_{1-3})$ being particularly preferred. Also preferred are acyclic saturated alkanylidene radicals in which the divalent radical is at a terminal carbon, e.g., methanylidene, ethan-1-ylidene, propan-1-ylidene, butan-1-ylidene, 2-methyl-propan-1-ylidene, and the like.

"Alkylidyne:" refers to a saturated or unsaturated, branched or straight-chain trivalent hydrocarbon radical derived by removal of three hydrogen atoms from the same carbon atom of a parent alkane, alkene or alkyne. The trivalent radical center forms a triple bond with a single atom. Typical alkylidyne radicals include, but are not limited to, methanylidyne; ethanylidyne; propylidynes such as propan-1-ylidyne, prop-2-en-1-ylidyne, prop-2-yn-1-ylidyne; butylidynes such as butan-1-ylidyne, 2-methyl-propan-1-ylidyne, but-2-en-1-ylidyne, but-3-en-1-ylidyne, buta-2,3-dien-1-ylidyne, but-2-yn-1-ylidyne, but-3-yn-1-ylidyne, etc.; and the like. Where specific levels of saturation are intended, the nomenclature alkanylidyne, alkenylidyne and/or alkynylidyne is used. In preferred embodiments, the alkylidyne group is $(C_{1-8})$ alkylidyne, with $(C_{1-3})$ being particularly preferred. Also preferred are saturated alkanylidyne radicals, e.g., methanylidyne, ethanylidyne, propan-1-ylidyne, butan-1-ylidyne, 2-methyl-propan-1-ylidyne, and the like.

"Heteroalkyl, Heteroalkanyl, Heteroalkenyl, Heteroalkynyl, Heteroalkylidene, Heteroalkylidyne, Heteroalkyldiyl, Vic Heteralkyldiyl, Gem Heteroalkyldiyl, Heteroalkyleno and Heteroalkyldiylidene:" refer to alkyl, alkanyl, alkenyl, alkynyl, alkylidene, alkylidyne, alkyldiyl, vic alkyldiyl, gem alkyldiyl, alkyleno and alkyldiylidene radicals, respectively, in which one or more carbon atoms (and any necessary associated hydrogen atoms) are independently replaced with the same or different heteroatoms (including any necessary hydrogen or other atoms). Typical heteroatoms to replace the carbon atom(s) include, but are not limited to, N, P, O, S, Si, etc. Preferred heteroatoms are O, N and S. Thus, heteroalkyl, heteroalkanyl, heteroalkenyl, heteroalkynyl, heteroalkylidene, heteroalkylidyne, heteroalkyldiyl, vic heteroalkyldiyl, gem heteroalkyldiyl, heteroalkyleno and heteroalkyldiylidene radicals can contain one or more of the same or different heteroatomic groups, including, by way of example and not limitation, epoxy (—O—), epidioxy (—O—O—), thioether (—S—), epidithio (—SS—), epoxythio (—O—S—), epoxyimino (—O—NR'—), imino (—NR'—), biimmino (—NR'—NR'—), azino (=N—N=), azo (—N=N—), azoxy (—N—O—N—), azimino (—NR'—N=N—), phosphano (—PH—), $\lambda^4$-sulfano (—SH$_2$-), sulfonyl (—S(O)$_2$—), and the like, where each R' is independently hydrogen or (C$_1$-C$_6$) alkyl.

"Parent Aromatic Ring System:" refers to an unsaturated cyclic or polycyclic ring system having a conjugated π electron system. Specifically included within the definition of "parent aromatic ring system" are fused ring systems in which one or more rings are aromatic and one or more rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like "Aryl:" refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is (C$_{5-20}$) aryl, with (C$_{5-10}$) being particularly preferred. Particularly preferred aryl groups are phenyl and naphthyl groups.

"Arylalkyl:" refers to an acyclic alkyl group in which one of the hydrogen atoms bonded to a carbon atom, typically a terminal carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. [In preferred embodiments, the arylalkyl group is (C$_{6-26}$) arylalkyl, e.g., the alkanyl, alkenyl or alkynyl moiety of the arylalkyl group is (C$_{1-6}$) and the aryl moiety is (C$_{5-20}$). In particularly preferred embodiments the arylalkyl group is (C$_{6-13}$), e.g., the alkanyl, alkenyl or alkynyl moiety of the arylalkyl group is (C$_{1-3}$) and the aryl moiety is (C$_{5-10}$). Even more preferred arylalkyl groups are phenylalkanyls.

"Alkanyloxy:" refers to a saturated branched, straight-chain or cyclic monovalent hydrocarbon alcohol radical derived by the removal of the hydrogen atom from the hydroxide oxygen of the alcohol. Typical alkanyloxy groups include, but are not limited to, methanyl; ethanyloxy; propanyloxy groups such as propan-1-yloxy (CH$_3$CH$_2$CH$_2$O—), propan-2-yloxy ((CH$_3$)$_2$CHO—), cyclopropan-1-yloxy, etc.; butyanyloxy groups such as butan-1-yloxy, butan-2-yloxy, 2-methyl-propan-1-yloxy, 2-methyl-propan-2-yloxy, cyclobutan-1-yloxy, etc.; and the like. In preferred embodiments, the alkanyloxy groups are (C$_{1-8}$) alkanyloxy groups, with (C$_{1-3}$) being particularly preferred.

"Parent Heteroaromatic Ring System:" refers to a parent aromatic ring system in which one or more carbon atoms are each independently replaced with a heteroatom. Typical heteratoms to replace the carbon atoms include, but are not limited to, N, P, O, S, Si etc. Specifically included within the definition of "parent heteroaromatic ring systems" are fused ring systems in which one or more rings are aromatic and one or more rings are saturated or unsaturated, such as, for example, arsindole, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl:" refers to a monovalent heteroaromatic radical derived by the removal of one hydrogen atom from a single atom of a parent heteroaromatic ring system. Typical heteroaryl groups include, but are not limited to, radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-20 membered heteroaryl, with 5-10 membered heteroaryl being particularly preferred. Specific preferred heteroaryls for the present invention are quinoline, isoquinoline, pyridine, pyrimidine, furan, thiophene and imidazole.

"Substituted:" refers to a radical in which one or more hydrogen atoms are each independently replaced with the same or different substituent(s). Typical substituents include, but are not limited to, —X, —R, —O$^-$—, =O, —OR, —O—OR, —SR, —S$^-$, =S, —NRR, =NR, —CX$_3$, —CN, —OCN, —SCN, —NCO, —NCS, —NO, —NO$_2$, =N$_2$, —N$_3$, —NHOH, —S(O)$_2$O$^-$—, —S(O)$_2$OH, —S(O)$_2$R, —P(O)(O$^-$)$_2$, —P(O)(OH)$_2$, —C(O)R, —C(O)X, —C(S)R, —C(S)X, —C(O)OR, —C(O)O$^-$, —C(S)OR, —C(O)SR, —C(S)SR, —C(O)NRR, —C(S)NRR and —C(NR)NRR, where each X is independently a halogen (preferably —F, —Cl or —Br) and each R is independently —H, alkyl, alkanyl, alkenyl, alkynyl, alkylidene, alkylidyne, aryl, arylalkyl, arylheteroalkyl, heteroaryl, heteroarylalkyl or heteroaryl-heteroalkyl, as defined herein. Preferred substituents include hydroxy, halogen, C$_{1-8}$alkyl, C$_{1-8}$alkanyloxy, fluorinated alkanyloxy, fluorinated alkyl, C$_{1-8}$alkylthio, C$_{3-8}$cycloalkyl, C$_{3-8}$cycloalkanyloxy, nitro, amino, C$_{1-8}$alkylamino, C$_{1-8}$dialkylamino, C$_{3-8}$cycloalkylamino, cyano, carboxy, C$_{1-7}$alkanyloxycarbonyl, C$_{1-7}$alkylcarbonyloxy, formyl, carbamoyl, phenyl, aroyl, carbamoyl, amidino, ($C_{1-8}$alkylamino)carbonyl, (arylamino)carbonyl and aryl($C_{1-8}$alkyl)carbonyl.

"Aroyl" refers to arylacyl substituents.

"Acyl" refers to alkylcarbonyl substituents.

With reference to substituents, the term "independentlyl" means that when more than one of such substituent is possible, such substituents may be the same or different from each other.

Throughout this disclosure, the terminal portion of the designated side chain is described first, followed by the adjacent functionality toward the point of attachment. Thus, for example, a "phenyl$C_{1-6}$alkanylaminocarbonyl$C_{1-6}$alkyl" substituent refers to a group of the formula

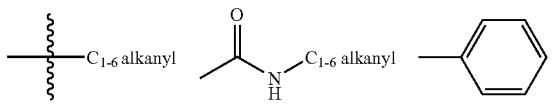

The invention is directed compounds of formula (I)

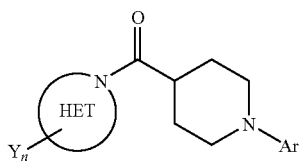

wherein

is a 4 to 8 membered cyclic heteroalkyl group bonded to the rest of the molecule through a ring nitrogen atom and optionally containing 1-2 heteroatoms in addition to said ring nitrogen atom, wherein the optional 1-2 additional heteroatoms are independently selected from the group consisting of N, O and S; or a 5 to 10 membered heteroaryl group bonded to the rest of the molecule through a ring nitrogen atom and selected from the group consisting of dihydroquinoline, tetrahydroquinoline, dihydroisoquinoline, tetrahydroisoquinoline, benzimidazole, imidazole, imidazoline, indazole, indole, indoline, isoindole, isoindoline, pyrazole, pyrrole, and triazole;

Y is bonded to

at a substitutable atom and is independently selected from the group consisting of hydrogen; hydroxyl; $R^1$; $R^1O$—; $R^1S$—; $CF_3O$—; $R^1S(O)$—; $R^1SO_2$—; -LCOX; $C_{6-10}$aryl; a 3 to 7 membered cyclic heteroalkanyl containing from 1 to 3 heteroatoms wherein said heteroatoms independently are N, O or S; and a 5 to 10 membered heteroaryl selected from the group consisting of benzofuran, benzimidazole, benzisoxazole, benzthiazole, benzothiophene, benzoxazole, cinnoline, furan, imidazole, imidazoline, indazole, indole, indoline, indolizine, isobenzofuran, isoindole, isoindoline, isoquinoline, isothiazole, isoxazole, naphthyridine, oxadiazole, oxazole, pthalazine, pteridine, purine, pyran, pyrazine, pyrazole, pyridazine, pyridine, pyrimidine, pyrrole, pyrrolizine, quinoline, quinolizine, quinazoline, quinoxaline, tetrazole, thiadiazole, thiazole, thiophene, triazine, and triazole;

n is an integer from 0 to 4;

Ar is phenyl; naphthyl; a 5-6 membered heteroaryl ring selected from the group consisting of furan, imidazole, isothiazole, isoxazole, oxadiazole, oxazole, pyran, pyrazine, pyrazole, pyridazine, pyrrole, tetrazole, thiadiazole, triazine, and triazole; or a fused 5,6 or 6,6 heteroaryl selected from the group consisting of benzimidazole, benzisoxazole, benzofuran, benzoxazole, benzthiazole, benzothiophene, cinnoline, indazole, indole, indoline, indolizine, isobenzofuran, isoindole, isoindoline, isoquinoline, naphthyridine, pthalazine, pteridine, pyrrolizine, quinoline, and quinolizine; wherein Ar is optionally substituted with one to four substituents independently selected from the group consisting of halogen; $R^1$; fluorinated $C_{1-10}$alkyl; phenyl; amino; cyano; fluorinated $C_{1-10}$alkyl; a 3 membered cyclic heteroalkyl containing 1 heteroatom that is N, O or S wherein said 3 membered cyclic heteroalkyl is optionally substituted with a substituent that is halogen, $R^1$, fluorinated $C_{1-10}$alkyl, amino, cyano, $R^1O$—, $R^1S$—, $R^1SO_2$—, $R^1S(O)$—, $R^1SO_2NH$—, or -LCOX; a 4 to 5 membered cyclic heteroalkyl containing 1-3 heteroatoms that independently are N, O or S wherein said 4 to 5 membered cyclic heteroalkyl is optionally substituted with 1 to 2 substituents that independently are halogen, $R^1$, fluorinated $C_{1-10}$alkyl, amino, cyano, $CF_3O$—, $R^1O$—, $R^1S$—, $R^1SO_2$—, $R^1S(O)$—, $R^1SO_2NH$—, or -LCOX; a 6 to 7 membered cyclic heteroalkyl containing 1-3 heteroatoms that independently are N, O or S wherein said 6 to 7 membered cyclic heteroalkyl is optionally substituted with 1 to 3 substituents that independently are halogen, $R^1$, fluorinated $C_{1-10}$alkyl, amino, cyano, $R^1O$—, $R^1S$—, $R^1SO_2$—, $R^1S(O)$—, $R^1SO_2NH$—, or -LCOX; a heteroaryl wherein said heteroaryl is cinnoline, furan, imidazole, indazole, indole, indoline, indolizine, isobenzofuran, isoindole, isoindoline, isoquinoline, isothiazole, isoxazole, naphthyridine, oxadiazole, oxazole, pthalazine, pteridine, pyran, pyrazine, pyrazole, pyridazine, pyridine, pyrimidine, pyrrole, pyrrolizine, quinoline, quinolizine, quinazoline, quinoxaline, tetrazole, thiadiazole, triazine, or triazole wherein said heteroaryl is optionally substituted with 1 to 3 substituents that independently are halogen, $R^1$, fluorinated $C_{1-10}$alkyl, amino, cyano, $CF_3O$—, $R^1O$—, $R^1S$—, $R^1SO_2$—, $R^1S(O)$—, $R^1SO_2NH$—, or -LCOX;; hydroxyl;; $R^1O$—; $R^1S$—; $R^1SO_2$—; $R^1S(O)$—; $R^1SO_2NH$—; -LCOX; and $C_{6-10}$aryl;

$R^1$ is $C_{1-10}$alkyl;

L is —NH—, a direct bond, —O—, or —$CH_2$—;

X is H, $R^1$, HO, $R^1O$—, $R^1S$—, —$NH_2$, $R^1NH$—, or $(R^1)_2N$—; and enantiomers, diastereomers, tautomers, solvates, and pharmaceutically acceptable salts thereof.

Embodiments of the present invention are compounds of formula (I) in which (a)  is thiomorpholin-4-yl;

(b)  is morpholin-4-yl;

(c) 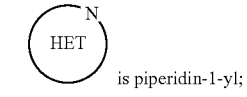 is piperidin-1-yl;

(d) 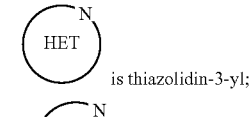 is thiazolidin-3-yl;

(e)  is azepan-1-yl;

(f) 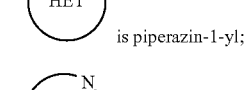 is piperazin-1-yl;

(g) 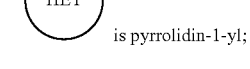 is pyrrolidin-1-yl;

(h) Y is OH;
(i) Y is methylcarbonyl;
(j) Y is methyl;
(k) n is 0;
(l) n is 1;
(m) Ar is phenyl;
(n) Ar is naphthyl;
(o) Ar is substituted with 1-2 substituents independently selected from the group consisting of halogen, $R^1$, $R^1O-$, fluorinated $C_{1-10}$alkyl, phenyl, and fluorinated $C_{1-10}$alkyl;
(p) Ar is substituted with 1-2 substituents independently selected from the group consisting of methyl, phenyl, $CF_3-$, F, and $CH_3O-$; and
(q) combinations of (a) through (p), above.

Thus, an embodiment of the present invention include a compound of formula (I) wherein Ar is phenyl optionally substituted with 1-2 substituents independently selected from the group consisting of halogen, $R^1$, $R^1O-$, fluorinated $C_{1-10}$alkyl, phenyl, and fluorinated $C_{1-10}$alkyl.

Another embodiment of the present invention is a compound of formula (I) wherein

 is piperidin-1-yl and n is 1.

Another embodiment of the present invention is a compound of formula (I) wherein n is 1 and Y is OH or methylcarbonyl.

Another embodiment of the present invention is a compound of formula (I) wherein Ar is biphenyl, methylphenyl or dimethylphenyl;

Another embodiment of the present invention is a compound of formula (I) selected from the group consisting of:
Thiomorpholin-4-yl-(1-o-tolyl-piperidin-4-yl)-methanone;
[1-(2,3-Dimethyl-phenyl)-piperidin-4-yl]-(4-hydroxy-piperidin-1-yl)-methanone;
(1-Biphenyl-3-yl-piperidin-4-yl)-morpholin-4-yl-methanone;
[1-(3-Fluoro-4-methyl-phenyl)-piperidin-4-yl]-thiomorpholin-4-yl-methanone
Morpholin-4-yl-[1-(3-trifluoromethyl-phenyl)-piperidin-4-yl]-methanone;
[1-(3,4-Dimethyl-phenyl)-piperidin-4-yl]-thiomorpholin-4-yl-methanone;
[1-(2,3-Dimethyl-phenyl)-piperidin-4-yl]-thiomorpholin-4-yl-methanone;
[1-(3,4-Dimethyl-phenyl)-piperidin-4-yl]-(4-hydroxy-piperidin-1-yl)-methanone;
[1-(3,4-Dimethyl-phenyl)-piperidin-4-yl]-piperidin-1-yl-methanone;
[1-(3-Fluoro-4-methyl-phenyl)-piperidin-4-yl]-piperidin-1-yl-methanone;
(4-Hydroxy-piperidin-1-yl)-(1-o-tolyl-piperidin-4-yl)-methanone;
[1-(3,4-Dimethyl-phenyl)-piperidin-4-yl]-morpholin-4-yl-methanone;
Morpholin-4-yl-(1-o-tolyl-piperidin-4-yl)-methanone;
[1-(2,3-Dimethyl-phenyl)-piperidin-4-yl]-piperidin-1-yl-methanone;
[1-(3,5-Difluoro-phenyl)-piperidin-4-yl]-morpholin-4-yl-methanone;
[1-(2,3-Dimethyl-phenyl)-piperidin-4-yl]-thiazolidin-3-yl-methanone;
(1-Naphthalen-1-yl-piperidin-4-yl)-piperidin-1-yl-methanone;
[1-(3,5-Difluoro-phenyl)-piperidin-4-yl]-thiomorpholin-4-yl-methanone;
[1-(3-Fluoro-4-methyl-phenyl)-piperidin-4-yl]-morpholin-4-yl-methanone;
[1-(3,5-Difluoro-phenyl)-piperidin-4-yl]-piperidin-1-yl-methanone;
(1-Biphenyl-3-yl-piperidin-4-yl)-thiomorpholin-4-yl-methanone;
[1-(3-Fluoro-4-methyl-phenyl)-piperidin-4-yl]-(4-hydroxy-piperidin-1-yl)-methanone;
[1-(3,5-Difluoro-phenyl)-piperidin-4-yl]-(4-hydroxy-piperidin-1-yl)-methanone;
(1-Naphthalen-1-yl-piperidin-4-yl)-thiazolidin-3-yl-methanone;
Azepan-1-yl-(1-o-tolyl-piperidin-4-yl)-methanone;
Piperidin-1-yl-(1-o-tolyl-piperidin-4-yl)-methanone;
[1-(3-Methoxy-phenyl)-piperidin-4-yl]-morpholin-4-yl-methanone;
Piperidin-1-yl-[1-(3-trifluoromethyl-phenyl)-piperidin-4-yl]-methanone;
Piperidin-1-yl-(1-m-tolyl-piperidin-4-yl)-methanone;
1-[4-(1-Biphenyl-3-yl-piperidine-4-carbonyl)-piperazin-1-yl]-ethanone;
1-{4-[1-(2,3-Dimethyl-phenyl)-piperidine-4-carbonyl]-piperazin-1-yl}-ethanone;
Morpholin-4-yl-(1-m-tolyl-piperidin-4-yl)-methanone;
(1-Biphenyl-3-yl-piperidin-4-yl)-piperidin-1-yl-methanone;
[1-(3-Methoxy-phenyl)-piperidin-4-yl]-thiomorpholin-4-yl-methanone;

[1-(2,3-Dimethyl-phenyl)-piperidin-4-yl]-(2,6-dimethyl-piperidin-1-yl)-methanone;
[1-(2,3-Dimethyl-phenyl)-piperidin-4-yl]-(3-hydroxy-pyrrolidin-1-yl)-methanone;
Thiazolidin-3-yl-(1-o-tolyl-piperidin-4-yl)-methanone;
Pyrrolidin-1-yl-(1-o-tolyl-piperidin-4-yl)-methanone;
(1-Isoquinolin-1-yl-piperidin-4-yl)-morpholin-4-yl-methanone;
[1-(3,6-Dimethyl-pyrazin-2-yl)-piperidin-4-yl]-morpholin-4-yl-methanone;
Morpholin-4-yl-(1-naphthalen-1-yl-piperidin-4-yl)-methanone;
[1-(2,3-Dimethyl-phenyl)-piperidin-4-yl]-morpholin-4-yl-methanone;
Morpholin-4-yl-[1-(3-trifluoromethyl-phenyl)-piperidin-4-yl]-methanone;
(1-Naphthalen-1-yl-piperidin-4-yl)-thiomorpholin-4-yl-methanone;
(1-Isoquinolin-1-yl-piperidin-4-yl)-thiomorpholin-4-yl-methanone;
Thiomorpholin-4-yl-(1-m-tolyl-piperidin-4-yl)-methanone;
Thiomorpholin-4-yl-[1-(3-trifluoromethyl-phenyl)-piperidin-4-yl]-methanone;
[1-(3,6-Dimethyl-pyrazin-2-yl)-piperidin-4-yl]-thiomorpholin-4-yl-methanone;
(4-Hydroxy-piperidin-1-yl)-(1-naphthalen-1-yl-piperidin-4-yl)-methanone;
(4-Hydroxy-piperidin-1-yl)-(1-isoquinolin-1-yl-piperidin-4-yl)-methanone;
(1-Biphenyl-3-yl-piperidin-4-yl)-(4-hydroxy-piperidin-1-yl)-methanone;
(1-Isoquinolin-1-yl-piperidin-4-yl)-piperidin-1-yl-methanone;
Piperidin-1-yl-(1-m-tolyl-piperidin-4-yl)-methanone;
[1-(3-Methoxy-phenyl)-piperidin-4-yl]-piperidin-1-yl-methanone;
Piperidin-1-yl-[1-(3-trifluoromethyl-phenyl)-piperidin-4-yl]-methanone;
[1-(3,6-Dimethyl-pyrazin-2-yl)-piperidin-4-yl]-piperidin-1-yl-methanone;
[1-(2,3-Dimethyl-phenyl)-piperidin-4-yl]-pyrrolidin-1-yl-methanone;
(1-Naphthalen-1-yl-piperidin-4-yl)-pyrrolidin-1-yl-methanone;
(1-Biphenyl-3-yl-piperidin-4-yl)-pyrrolidin-1-yl-methanone;
(1-Isoquinolin-1-yl-piperidin-4-yl)-pyrrolidin-1-yl-methanone;
[1-(3-Fluoro-4-methyl-phenyl)-piperidin-4-yl]-pyrrolidin-1-yl-methanone;
Pyrrolidin-1-yl-(1-m-tolyl-piperidin-4-yl)-methanone;
[1-(3,5-Difluoro-phenyl)-piperidin-4-yl]-pyrrolidin-1-yl-methanone;
[1-(3,6-Dimethyl-pyrazin-2-yl)-piperidin-4-yl]-pyrrolidin-1-yl-methanone;
[1-(3-Methoxy-phenyl)-piperidin-4-yl]-pyrrolidin-1-yl-methanone;
Pyrrolidin-1-yl-[1-(3-trifluoromethyl-phenyl)-piperidin-4-yl]-methanone;
(1-Biphenyl-3-yl-piperidin-4-yl)-thiazolidin-3-yl-methanone;
(1-Isoquinolin-1-yl-piperidin-4-yl)-thiazolidin-3-yl-methanone;
Thiazolidin-3-yl-(1-m-tolyl-piperidin-4-yl)-methanone;
[1-(3,5-Difluoro-phenyl)-piperidin-4-yl]-thiazolidin-3-yl-methanone;
[1-(3,6-Dimethyl-pyrazin-2-yl)-piperidin-4-yl]-thiazolidin-3-yl-methanone;
[1-(3-Methoxy-phenyl)-piperidin-4-yl]-thiazolidin-3-yl-methanone;
Thiazolidin-3-yl-[1-(3-trifluoromethyl-phenyl)-piperidin-4-yl]-methanone;
(2,6-Dimethyl-piperidin-1-yl)-(1-naphthalen-1-yl-piperidin-4-yl)-methanone;
(1-Biphenyl-3-yl-piperidin-4-yl)-(2,6-dimethyl-piperidin-1-yl)-methanone;
(2,6-Dimethyl-piperidin-1-yl)-(1-o-tolyl-piperidin-4-yl)-methanone;
(2,6-Dimethyl-piperidin-1-yl)-( 1-m-tolyl-piperidin-4-yl)-methanone;
[1-(3,5-Difluoro-phenyl)-piperidin-4-yl]-(2,6-dimethyl-piperidin-1-yl)-methanone;
(2,6-Dimethyl-piperidin-1-yl)-[1-(3,6-dimethyl-pyrazin-2-yl)-piperidin-4-yl]-methanone;
(2,6-Dimethyl-piperidin-1-yl)-[1-(3-methoxy-phenyl)-piperidin-4-yl]-methanone;
(2,6-Dimethyl-piperidin-1-yl)-[1-(3-trifluoromethyl-phenyl)-piperidin-4-yl]-methanone;
(3-Hydroxy-pyrrolidin-1-yl)-(1-naphthalen-1-yl-piperidin-4-yl)-methanone;
(1-Biphenyl-3-yl-piperidin-4-yl)-(3-hydroxy-pyrrolidin-1-yl)-methanone;
(3-Hydroxy-pyrrolidin-1-yl)-(1-isoquinolin-1-yl-piperidin-4-yl)-methanone;
(3-Hydroxy-pyrrolidin-1-yl)-(1-o-tolyl-piperidin-4-yl)-methanone;
[1-(3-Fluoro-4-methyl-phenyl)-piperidin-4-yl]-(3-hydroxy-pyrrolidin-1-yl)-methanone;
[1-(3,6-Dimethyl-pyrazin-2-yl)-piperidin-4-yl]-(3-hydroxy-pyrrolidin-1-yl)-methanone;
Azepan-1-yl-[1-(2,3-dimethyl-phenyl)-piperidin-4-yl]-methanone;
Azepan-1-yl-(1-naphthalen-1-yl-piperidin-4-yl)-methanone;
Azepan-1-yl-(1-biphenyl-3-yl-piperidin-4-yl)-methanone;
Azepan-1-yl-(1-isoquinolin-1-yl-piperidin-4-yl)-methanone;
Azepan-1-yl-[1-(3-fluoro-4-methyl-phenyl)-piperidin-4-yl]-methanone;
Azepan-1-yl-(1-m-tolyl-piperidin-4-yl)-methanone;
Azepan-1-yl-[1-(3,5-difluoro-phenyl)-piperidin-4-yl]-methanone;
Azepan-1-yl-[1-(3-methoxy-phenyl)-piperidin-4-yl]-methanone;
Azepan-1-yl-[1-(3-trifluoromethyl-phenyl)-piperidin-4-yl]-methanone;
Azepan-1-yl-[1-(3,6-dimethyl-pyrazin-2-yl)-piperidin-4-yl]-methanone;
1-[4-(1-Isoquinolin-1-yl-piperidine-4-carbonyl)-piperazin-1-yl]-ethanone;
1-[4-(1-o-Tolyl-piperidine-4-carbonyl)-piperazin-1-yl]-ethanone;
1-{4-[1-(3-Fluoro-4-methyl-phenyl)-piperidine-4-carbonyl]-piperazin-1-yl}-ethanone;
1-[4-(1-m-Tolyl-piperidine-4-carbonyl)-piperazin-1-yl]-ethanone;
1-{4-[1-(3,5-Difluoro-phenyl)-piperidine-4-carbonyl]-piperazin-1-yl}-ethanone;
1-{4-[1-(3-Methoxy-phenyl)-piperidine-4-carbonyl]-piperazin-1-yl}-ethanone;
1-{4-[1-(3-Trifluoromethyl-phenyl)-piperidine-4-carbonyl]-piperazin-1-yl}-ethanone;

1-{4-[1-(3,6-Dimethyl-pyrazin-2-yl)-piperidine-4-carbonyl]-piperazin-1-yl}-ethanone;
1-[1-(2,3-Dimethyl-phenyl)-piperidine-4-carbonyl]-pyrrolidine-2-carboxylic acid amide;
1-(1-Naphthalen-1-yl-piperidine-4-carbonyl)-pyrrolidine-2-carboxylic acid amide;
1-(1-Biphenyl-3-yl-piperidine-4-carbonyl)-pyrrolidine-2-carboxylic acid amide;
1-(1-Isoquinolin-1-yl-piperidine-4-carbonyl)-pyrrolidine-2-carboxylic acid amide;
1-(1-o-Tolyl-piperidine-4-carbonyl)-pyrrolidine-2-carboxylic acid amide;
1-[1-(3-Fluoro-4-methyl-phenyl)-piperidine-4-carbonyl]-pyrrolidine-2-carboxylic acid amide;
1-(1-m-Tolyl-piperidine-4-carbonyl)-pyrrolidine-2-carboxylic acid amide;
1-[1-(3-Methoxy-phenyl)-piperidine-4-carbonyl]-pyrrolidine-2-carboxylic acid amide;
1-[1-(3-Trifluoromethyl-phenyl)-piperidine-4-carbonyl]-pyrrolidine-2-carboxylic acid amide;
1-[1-(3,5-Difluoro-phenyl)-piperidine-4-carbonyl]-pyrrolidine-2-carboxylic acid amide;
1-[1-(3,6-Dimethyl-pyrazin-2-yl)-piperidine-4-carbonyl]-pyrrolidine-2-carboxylic acid amide;
Azetidin-1-yl-[1-(2,3-dimethyl-phenyl)-piperidin-4-yl]-methanone;
Azetidin-1-yl-(1-naphthalen-1-yl-piperidin-4-yl)-methanone;
Azetidin-1-yl-(1-isoquinolin-1-yl-piperidin-4-yl)-methanone;
Azetidin-1-yl-(1-biphenyl-3-yl-piperidin-4-yl)-methanone;
Azetidin-1-yl-(1-o-tolyl-piperidin-4-yl)-methanone;
Azetidin-1-yl-[1-(3-fluoro-4-methyl-phenyl)-piperidin-4-yl]-methanone;
Azetidin-1-yl-(1-m-tolyl-piperidin-4-yl)-methanone;
Azetidin-1-yl-[1-(3-methoxy-phenyl)-piperidin-4-yl]-methanone;
Azetidin-1-yl-[1-(3-trifluoromethyl-phenyl)-piperidin-4-yl]-methanone;
Azetidin-1-yl-[1-(3,5-difluoro-phenyl)-piperidin-4-yl]-methanone;
Azetidin-1-yl-[1-(3,6-dimethyl-pyrazin-2-yl)-piperidin-4-yl]-methanone;
(2,6-Dimethyl-morpholin-4-yl)-[1-(2,3-dimethyl-phenyl)-piperidin-4-yl]-methanone;
(3,4-Dihydro-2H-quinolin-1-yl)-[1-(2,3-dimethyl-phenyl)-piperidin-4-yl]-methanone;
[1-(2,3-Dimethyl-phenyl)-piperidin-4-yl]-(4-ethyl-piperazin-1-yl)-methanone.

The compounds of the present invention may also be present in the form of pharmaceutically acceptable salts. For use in medicine, the salts of the compounds of this invention refer to non-toxic "pharmaceutically acceptable salts" (*Ref. International J. Pharm.*, 1986, 33, 201-217; *J. Pharm. Sci.*, January 1997, 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of the present invention (including their pharmaceutically acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected perenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

A therapeutically effective amount for use of the instant compounds or a pharmaceutical composition thereof comprises a dose range of from about 0.001 mg to about 1,000 mg, in particular from about 0.1 mg to about 500 mg or, more particularly from about 1 mg to about 250 mg of active ingredient per day for an average (70 kg) human.

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as vanilloid receptor modulators is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. As modulators of the vanilloid VR1 ion channel, the compounds of Formula (I) are useful in methods for treating or preventing a disease or condition in a mammal which disease or condition is affected by the modulation of one or more vanilloid receptors.

As modulators of the vanilloid VR1 ion channel, the compounds of Formula (I) are useful in methods for treating or preventing a disease or condition in a mammal which disease or condition is affected by the modulation of one or more vanilloid receptors. Such methods comprises administering to a mammal in need of such treatment or prevention a therapeutically effective amount of a compound, salt or solvate of Formula (I). In particular, the compounds of Formula (I) are useful for in methods for preventing or treating a chronic- or acute-pain causing diseases or conditions and pulmonary dysfunction, and more particularly, in treating diseases or conditions that cause inflammatory pain, burning pain, itch or urinary incontinence, and chronic obstructive pulmonary disease.

By way of example only, the compounds of Formula (I) are useful for treating diseases and conditions selected from the group consisting of osteoarthritis, rheumatoid arthritis, fibromyalgia, migraine, headache, toothache, burn, sunburn, snake bite (in particular, venomous snake bite), spider bite, insect sting, neurogenic bladder, benign prostatic hypertrophy, interstitial cystitis, urinary tract infection, cough, asthma, chronic obstructive pulmonary disease, rhinitis, contact dermatitis/hypersensitivity, itch, eczema, anxiety, panic disorders, pharyngitis, mucositis, enteritis, cellulites, peripheral neuropathy, bilateral peripheral neuropathy, diabetic neuropathy, postherpetic neuralgia, trigeminal neuralgia, causalgia, sciatic neuritis, mandibular joint neuralgia, peripheral neuritis, polyneuritis, stump pain, phantom limb pain, bony fractures, post-operative ileus, irritable bowel syndrome, inflammatory bowel diseases such as Crohn's Disease and ulcerative colitis, cholecystitis, pancreatitis, postmastectomy pain syndrome, oral neuropathic pain, Charcot's pain, reflex sympathetic dystrophy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, sinus headache, tension headache, labor, childbirth, intestinal gas, menstruation, hot flash, cancer, and trauma.

While the present invention comprises compositions comprising one or more of the compounds of Formula (I), the present invention also comprises compositions comprising intermediates used in the manufacture of compounds of Formulae (I).

General Synthetic Methods

Compounds of formula (I) can be prepared by methods known to those who are skilled in the art. The following reaction schemes are only meant to represent examples of the invention and are in no way meant to be a limit of the invention.

The compounds of formula 1, wherein Ar, HET, and Yn are defined as above, may be synthesized as outlined by the general synthetic route illustrated in Scheme 1. In the first step, treatment of a commercially available isonipecotate ester 11 is coupled to an aromatic halide (ArX) to afford the N-aryl isonipecotic acid III. These reactions are generally performed in the presence of a palladium catalyst, an appropriate phosphine ligand, a solvent such as THF, a base such as sodium t-butoxide, and at a temperature of 25° C. to 150° C., preferably at 50-70° C. The next step involves treatment of acid III with a reagent such as oxalyl chloride, in a solvent such as methylene chloride, to prepare the reactive acid chloride intermediate IV. Treatment of the resulting acid chloride IV with an appropriate amine V provides the desired final compound 1. These reactions are generally performed in the presence of a solvent, such as methylene chloride, and a base, such as triethylamine, at a temperature of 0° C. to 150° C., preferably at 25° C. The aryl halides ArX, and amine reagents V, are either commercially available or can be prepared by methods known to those skilled in the art.

Scheme I

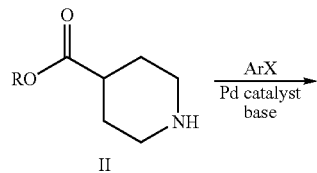

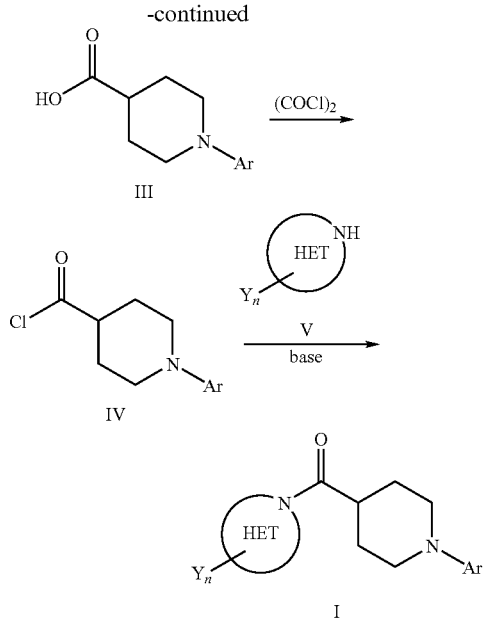

An alternative route to compounds of general formula I is illustrated in Scheme 2. Treatment of isonipecotic acid VI with an appropriate amine protecting group (PG) reagent, such as benzyl chloroformate, provides the N-protected isonipecotic acid VII. Treatment of the acid VII with oxalyl chloride, in the presence of a solvent such as methylene chloride, provides the reactive acid chloride intermediate VIII. Treatment of the resulting acid chloride VIII with an appropriate amine V provides the amide IX. These reactions are generally performed in the presence of a solvent, such as methylene chloride, and a base, such as triethylamine, at a temperature of 0° C. to 150° C., preferably from 0° C.-25° C. Removal of the amino protecting group (PG) under standard procedures provides the isonipecotic amide X. Coupling of an aromatic halide (ArX) to isonipecotic amide X affords the desired final product I. These reactions are generally performed in the presence of a palladium catalyst, an appropriate phosphine ligand, a solvent such as THF, a base such as sodium t-butoxide, and at a temperature of 25° C. to 150° C., preferably at 50-70° C. The aryl halides ArX, and amine reagents V, are either commercially available or can be prepared by methods known to those skilled in the art.

Scheme 2

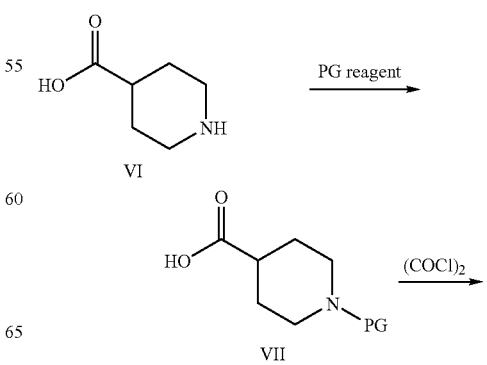

-continued

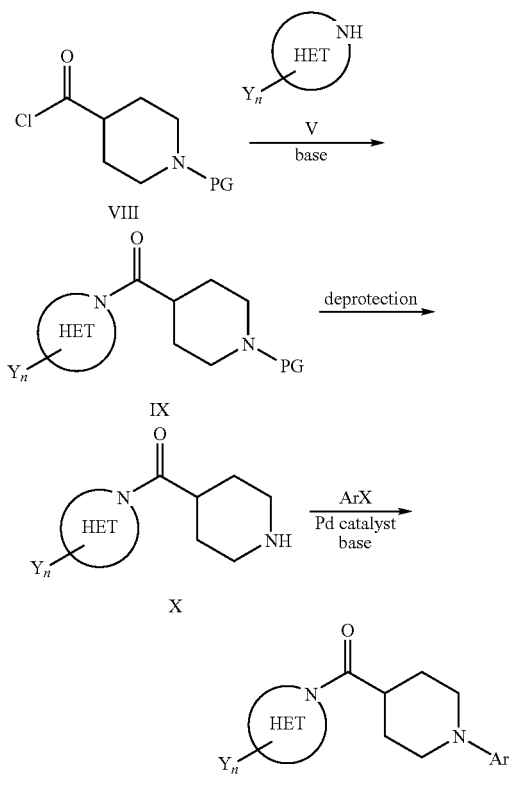

General Procedure A for N-Aryl Isonipecotic Acids

To a solution of aromatic halide (bromide or iodide) (0.1 mmol) in THF (1 mL) was added palladium acetate (2.3 mg, 0.001 (1%) mmol) and 2-(di-t-butylphosphino)biphenyl (6 mg, 0.002 (2%) mmol). The resulting solution was stirred at 25° C. for 5 minutes, then ethyl isonipecotate (1 mmol) and sodium t-butoxide (2.2 mmol) was added. The resulting mixture was stirred at 25° C. for 2 hours and then heated at 65° C. for 12 hours. Water (3 mL) was added and the resulting mixture was heated at 50° C. until there was no evidence of ester remaining. The crude mixture was extracted with ethyl acetate, the aqueous layer was acidified by the addition of 1M HCl, and the resulting acidic aqueous layer was extracted with ethyl acetate. The organic layer was dried over anhydrous sodium sulfate and concentrated in vacuo to provide the desired N-aryl isonipecotic acid without further purification.

General Procedure B for N-Aryl Isonipecotic Amides

To a solution of N-aryl isonipecotic acid (0.2 mmol) in dichloromethane (1 mL) was added a 2 M solution oxalyl chloride (0.2 mL) in dichloromethane. The resulting mixture was stirred at 25° C. for 4 hr, concentrated in vacuo, and then re-dissolved in dichloromethane (0.2 mL). The resulting solution was added to a mixture of an appropriate secondary amine (0.2 mmol) and triethylamine (0.5 mmol) in dichloromethane (0.5 mL). The combined solution was stirred at 25° C. for 16 hours, poured into water, and extracted with dichloromethane. The combined organic layers were washed sequentially with 1 M HCl, 2 M Na$_2$CO$_3$, then dried over anhydrous sodium sulfate, and concentrated in vacuo. The resulting crude product was purified by preparative TLC using a 3:1 hexane/ethyl acetate solvent gradient to provide the desired N-aryl isonipecotic amides.

EXAMPLE 1

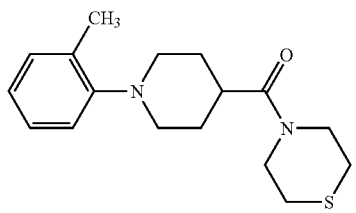

(1-o-Tolyl-piperidin-4-yl)-thiomorpholin-4-yl-methanone

The title compound was prepared from commercially available ethyl isonipecotate, o-tolyl bromide as the aryl halide, and thiomorpholine as the secondary amine utilizing general procedures A and B described above. $^1$H NMR (300 MHz, CDCl$_3$) δ 7.19-7.13 (m, 2H), 7.00-6.95 (m, 2H), 3.95 (m, 2H), 3.82 (m, 2H), 3.21 (m, 1H), 3.17 (m, 1H), 2.71-2.54 (m, 7H), 2.30 (s, 3H), 2.09 (dd, J=3.6, 13.1 Hz, 1H), 2.00 (dd, J=3.6, 12.0 Hz, 1H), 1.79 (m, 1H), 1.75 (m, 1H). ESI MS: 305.3 (MH$^+$).

EXAMPLE 2

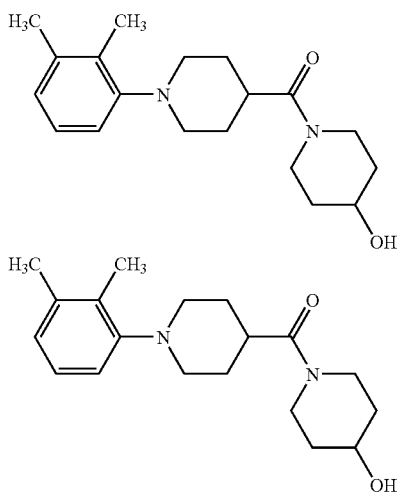

[1-(2,3-Dimethyl-phenyl)-piperidin-4-yl]-(4-hydroxy-piperidin-1-yl)-methanone

The title compound was prepared from commercially available ethyl isonipecotate, 2,3-dimethylbromobenzene as the aryl halide, and 4-hydroxypiperidine as the secondary amine utilizing general procedures A and B described above. ¹H NMR (300 MHz, CDCl₃) δ 7.06 (d, J=7.7 Hz, 1H), 6.90 (d, J=7.7 Hz, 2H), 4.12 (m, 1H), 3.96 (m, 1H), 3.83 (m, 1H), 3.33-3.13 (m, 4H), 2.70-2.61 (m, 3H), 2.27 (s, 3H), 2.22 (s, 3H), 2.12-1.43 (m, 8H). ESI MS: 317.4 (MH⁺).

EXAMPLE 3

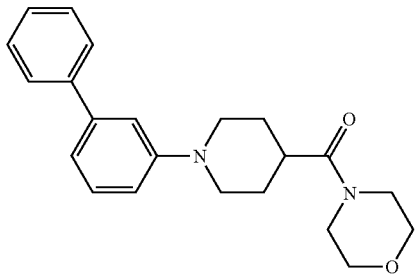

(1-Biphenyl-3-yl-piperidin-4-yl)-morpholin-4-yl-methanone

The title compound was prepared from commercially available ethyl isonipecotate, m-biphenyl bromide as the aryl halide, and morpholine as the secondary amine utilizing general procedures A and B described above. ¹H NMR (300 MHz, CDCl₃) δ 7.59-7.30 (m, 6H), 7.14 (t, J=2.0 Hz, 1H), 7.07 (d, J=7.7 Hz, 1H), 6.94 (dd, J=2.0, 7.6 Hz, 1H), 3.85 (m, 1H), 3.80 (m, 1H), 3.63-3.55 (m, 8H), 2.80 (dt, J=2.6, 12.2 Hz, 2H), 2.60 (tt, J=2.8, 11.4 Hz, 1H), 2.07 (dd, J=3.8, 12.8 Hz, 1H), 2.01 (dd, J=4.0, 12.0 Hz, 1H), 1.85 (m, 1H), 1.81 (m, 1H). ESI MS: 351.4 (MH⁺).

EXAMPLE 4

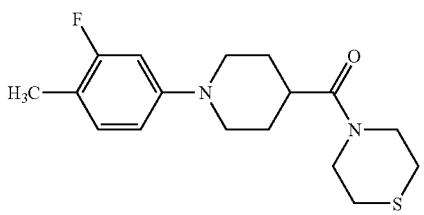

[1-(3-Fluoro-4-methyl-phenyl)-piperidin-4-yl]-thiomorpholin-4-yl-methanone

The title compound was prepared from commercially available ethyl isonipecotate, 3-fluoro-4-methylbromobenzene as the aryl halide, and thiomorpholine as the secondary amine utilizing general procedures A and B described above. ¹H NMR (300 MHz, CDCl₃) ¹H NMR (CDCl₃) δ 7.02 (dd, J=7.2, 9.2 Hz, 1H), 6.63-6.55 (m, 2H), 3.90 (m, 2H), 3.80 (m, 2H), 3.70 (m, 1H), 3.65 (m, 1H), 2.75-2.51 (m, 7H), 2.17 (d, J=1.6 Hz, 3H), 2.01 (dd, J=3.3, 13.4 Hz, 1H), 1.91 (dd, J=4.0, 11.4 Hz, 1H), 1.80 (m, 1H), 1.76 (m, 1H). ESI MS: 323.3 (MH⁺).

EXAMPLE 5

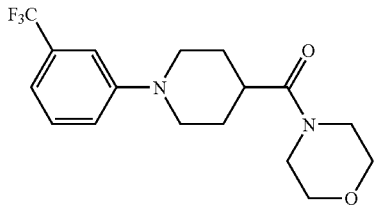

[1-(3-Trifluoromethyl-phenyl)-piperidin-4-yl]-morpholin-4-yl-methanone

The title compound was prepared from commercially available ethyl isonipecotate, 3-(trifluoromethyl)-bromobenzene as the aryl halide, and morpholine as the secondary amine utilizing general procedures A and B described above. ¹H NMR (300 MHz, CDCl₃) ¹H NMR (CDCl₃) δ 7.34 (dd, J=7.6, 8.6 Hz, 1H), 7.11-7.05 (m, 3H), 3.80 (m, 1H), 3.76 (m, 1H), 3.70-3.54 (m, 8H), 2.81 (dt, J=2.7, 12.4 Hz, 2H), 2.67-2.57 (m, 1H), 2.09 (dd, J=4.2, 13.4 Hz, 1H), 2.00 (dd, J=4.0, 11.7 Hz, 1H), 1.85 (m, 1H), 1.81 (m, 1H). ESI MS: 343.4 (MH⁺).

EXAMPLE 6

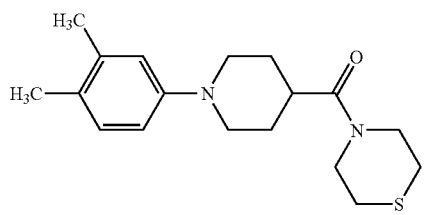

[1-(3,4-Dimethyl-phenyl)-piperidin-4-yl]-thiomorpholin-4-yl-methanone

The title compound was prepared from commercially available ethyl isonipecotate, 3,4-dimethylbromobenzene as the aryl halide, and thiomorpholine as the secondary amine utilizing general procedures A and B described above. ¹H NMR (300 MHz, CDCl₃) ¹H NMR (CDCl₃) δ 7.01 (d, J=7.8 Hz, 1H), 6.76 (d, J=2.3 Hz, 1H), 6.70 (dd, J=2.3, 7.8 Hz, 1H), 3.90 (m, 2H), 3.80 (m, 2H), 2.96 (m, 1H), 2.89 (m, 1H), 2.71-2.50 (m, 7H), 2.23 (s, 3H), 2.18 (s, 3H), 2.04 (dd, J=2.6, 12.2 Hz, 1H), 1.93 (dd, J=3.3, 12.3 Hz, 1H), 1.80 (m, 1H), 1.76 (m, 1H). ESI MS: 319.4 (MH⁺).

EXAMPLES 7-130

Using the methods and procedures of the schemes and examples, above, the compounds in Table 1 were synthesized.

TABLE 1

| Compound | Structure |
|---|---|
| 7 | (thiomorpholine-N-C(O)-piperidine-4-yl)-N-(2,3-dimethylphenyl)piperidine |
| 8 | (4-hydroxypiperidine-N-C(O)-piperidin-4-yl)-N-(3,4-dimethylphenyl)piperidine |
| 9 | (piperidine-N-C(O)-piperidin-4-yl)-N-(3,4-dimethylphenyl)piperidine |
| 10 | (piperidine-N-C(O)-piperidin-4-yl)-N-(3-fluoro-4-methylphenyl)piperidine |
| 11 | (4-hydroxypiperidine-N-C(O)-piperidin-4-yl)-N-(2-methylphenyl)piperidine |
| 12 | (morpholine-N-C(O)-piperidin-4-yl)-N-(3,4-dimethylphenyl)piperidine |
| 13 | (morpholine-N-C(O)-piperidin-4-yl)-N-(2-methylphenyl)piperidine |

TABLE 1-continued

| Compound | Structure |
|---|---|
| 14 | piperidine-C(O)-(1-(2,3-dimethylphenyl)piperidin-4-yl) |
| 15 | morpholine-C(O)-(1-(3,5-difluorophenyl)piperidin-4-yl) |
| 16 | thiazolidine-N-C(O)-(1-(2,3-dimethylphenyl)piperidin-4-yl) |
| 17 | piperidine-C(O)-(1-(naphthalen-1-yl)piperidin-4-yl) |
| 18 | thiomorpholine-C(O)-(1-(3,5-difluorophenyl)piperidin-4-yl) |
| 19 | morpholine-C(O)-(1-(3-fluoro-4-methylphenyl)piperidin-4-yl) |

TABLE 1-continued

| Compound | Structure |
|---|---|
| 20 | 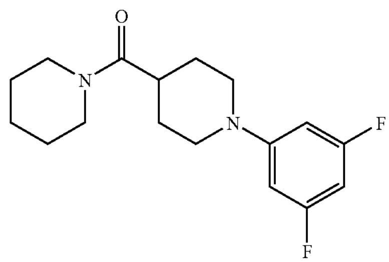 |
| 21 | 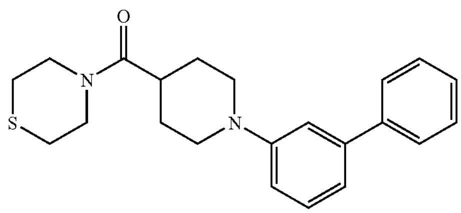 |
| 22 | 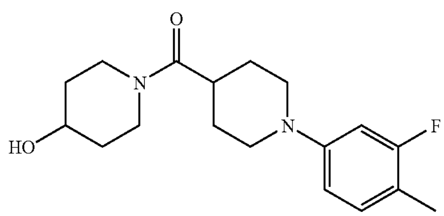 |
| 23 | 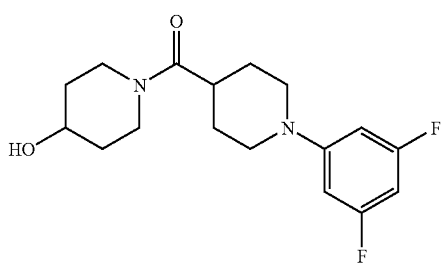 |
| 24 | 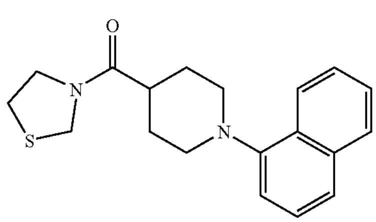 |
| 25 | 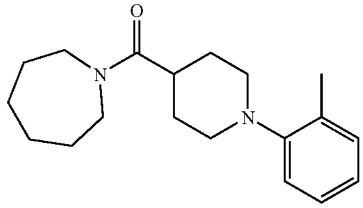 |

TABLE 1-continued

| Compound | Structure |
|---|---|
| 26 | 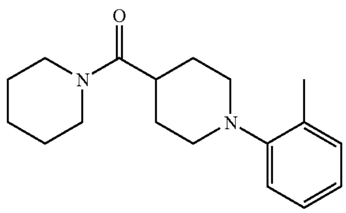 |
| 27 | 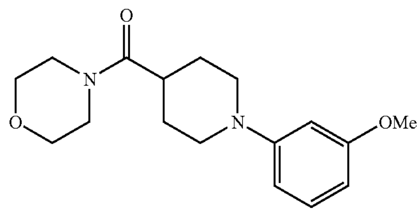 |
| 28 | 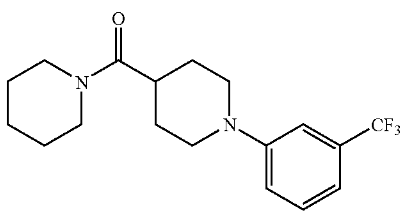 |
| 29 | 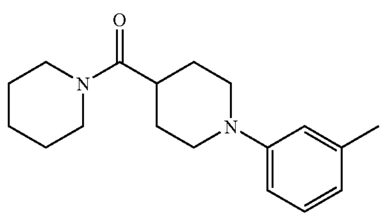 |
| 30 | 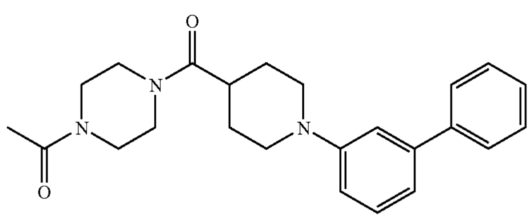 |
| 31 | 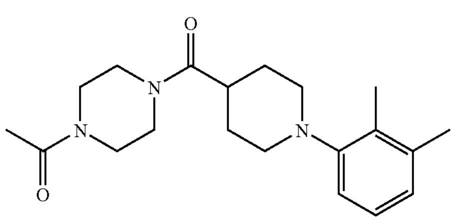 |
| 32 | 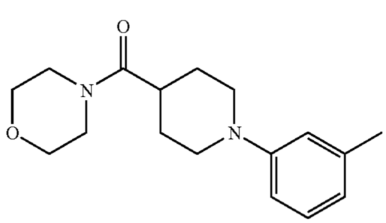 |

TABLE 1-continued

| Compound | Structure |
|---|---|
| 33 | 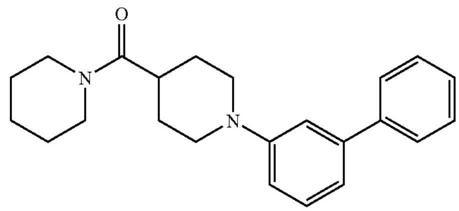 |
| 34 | 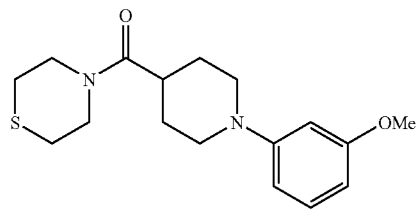 |
| 35 | 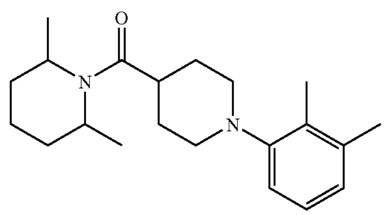 |
| 36 | 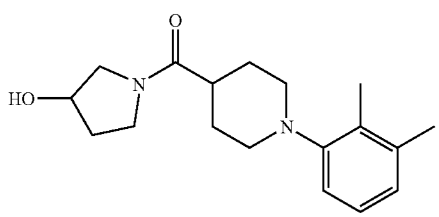 |
| 37 | 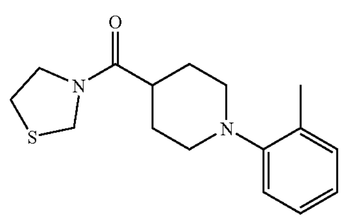 |
| 38 | 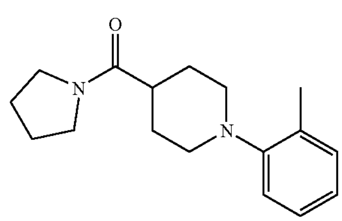 |
| 39 | 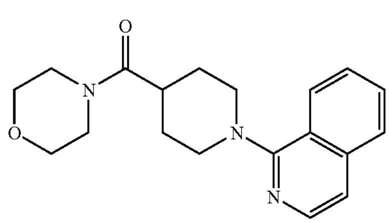 |

TABLE 1-continued
| Compound | Structure |
|---|---|
| 40 | 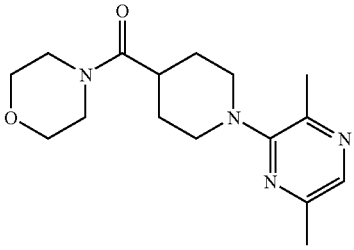 |
| 41 | 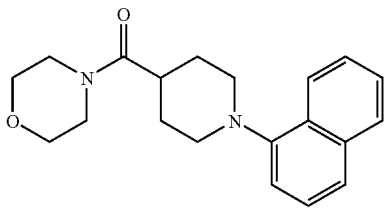 |
| 42 | 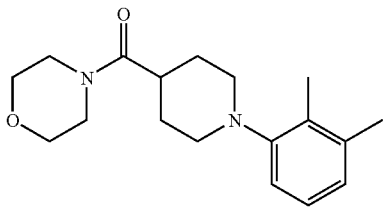 |
| 43 | 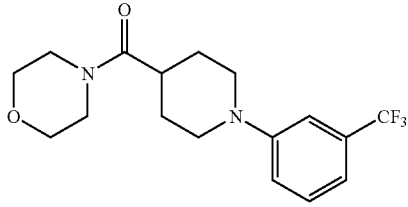 |
| 44 | 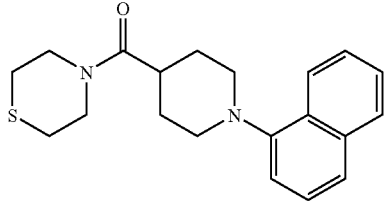 |
| 45 | 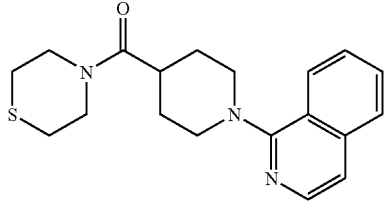 |
| 46 | 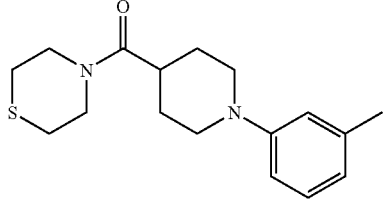 |

TABLE 1-continued
| Compound | Structure |
|---|---|
| 47 | 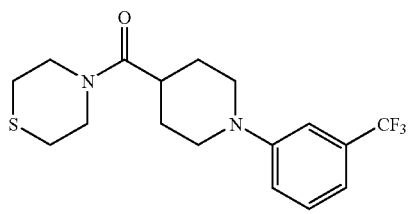 |
| 48 | 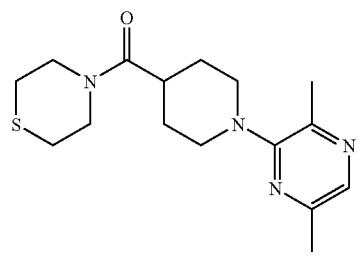 |
| 49 | 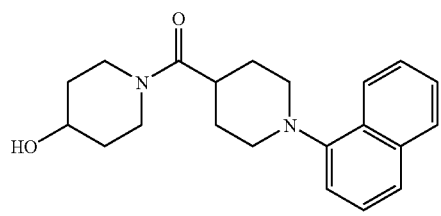 |
| 50 | 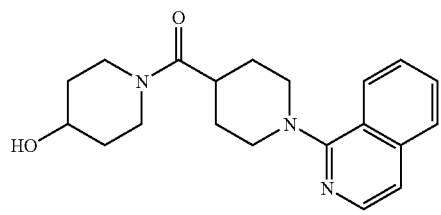 |
| 51 | 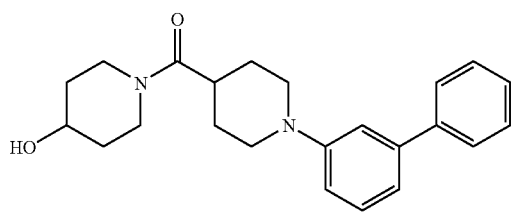 |
| 52 | 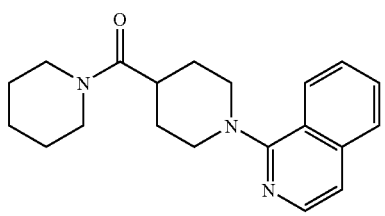 |

TABLE 1-continued

| Compound | Structure |
|---|---|
| 53 | 1-(3-methylphenyl)-4-(piperidine-1-carbonyl)piperidine |
| 54 | 1-(3-methoxyphenyl)-4-(piperidine-1-carbonyl)piperidine |
| 55 | 1-(3-trifluoromethylphenyl)-4-(piperidine-1-carbonyl)piperidine |
| 56 | 1-(3,6-dimethylpyrazin-2-yl)-4-(piperidine-1-carbonyl)piperidine |
| 57 | 1-(2,3-dimethylphenyl)-4-(pyrrolidine-1-carbonyl)piperidine |
| 58 | 1-(naphthalen-1-yl)-4-(pyrrolidine-1-carbonyl)piperidine |
| 59 | 1-(biphenyl-3-yl)-4-(pyrrolidine-1-carbonyl)piperidine |

TABLE 1-continued
| Compound | Structure |
|---|---|
| 60 | 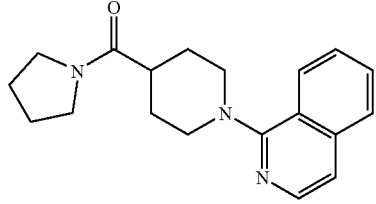 |
| 61 | 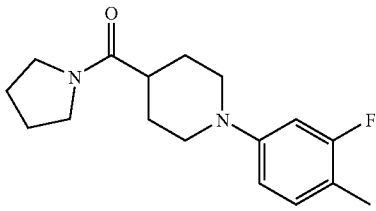 |
| 62 | 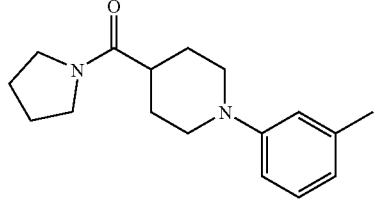 |
| 63 | 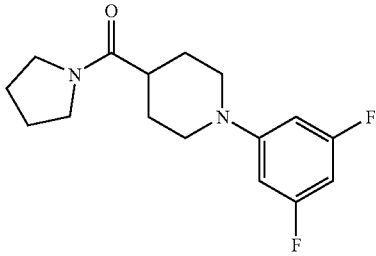 |
| 64 | 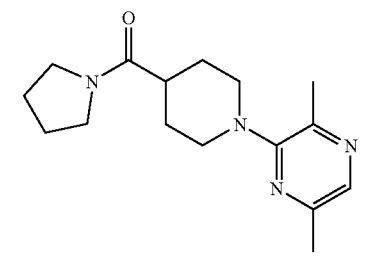 |
| 65 | 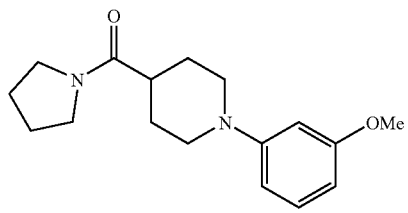 |

TABLE 1-continued
| Compound | Structure |
|---|---|
| 66 | 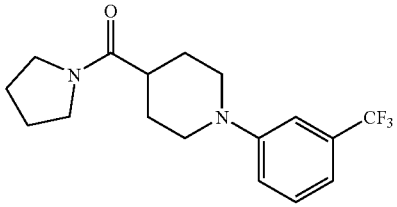 |
| 67 | 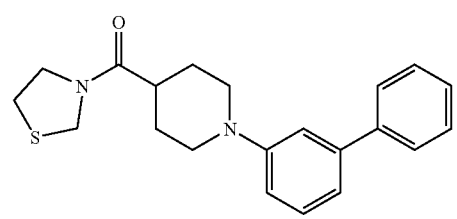 |
| 68 | 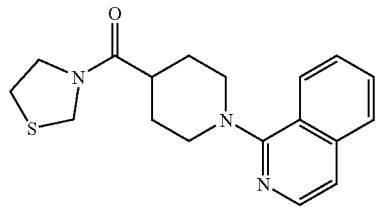 |
| 69 | 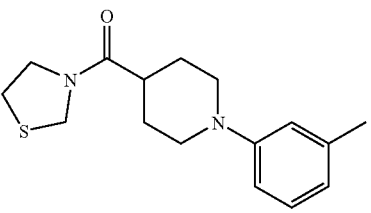 |
| 70 | 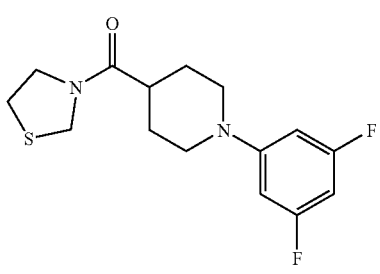 |
| 71 | 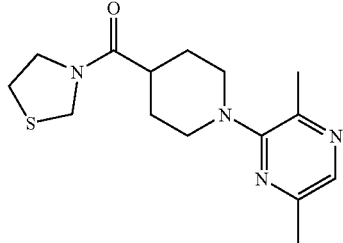 |

TABLE 1-continued

| Compound | Structure |
|---|---|
| 72 | 3-methoxyphenyl piperidine thiazolidine amide |
| 73 | 3-trifluoromethylphenyl piperidine thiazolidine amide |
| 74 | 1-naphthyl piperidine 2,6-dimethylpiperidine amide |
| 75 | 3-biphenyl piperidine 2,6-dimethylpiperidine amide |
| 76 | 2-methylphenyl piperidine 2,6-dimethylpiperidine amide |
| 77 | 3-methylphenyl piperidine 2,6-dimethylpiperidine amide |
| 78 | 3,5-difluorophenyl piperidine 2,6-dimethylpiperidine amide |

TABLE 1-continued

| Compound | Structure |
|---|---|
| 79 | 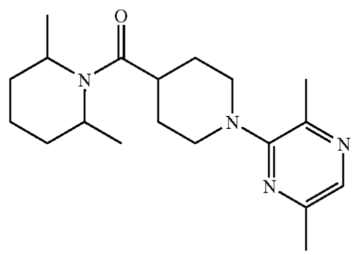 |
| 80 | 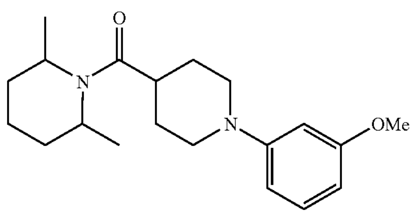 |
| 81 | 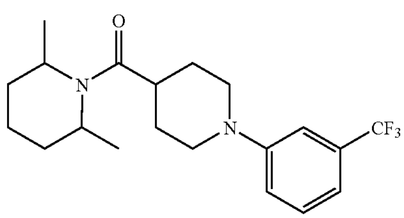 |
| 82 | 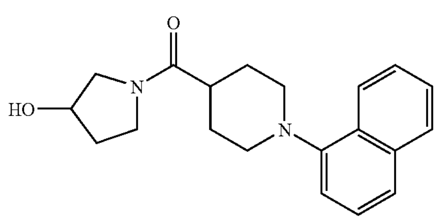 |
| 83 | 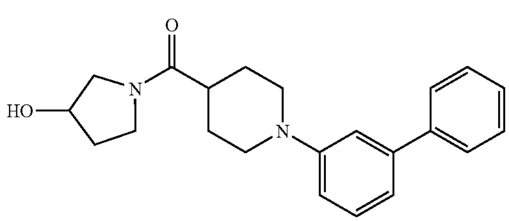 |
| 84 | 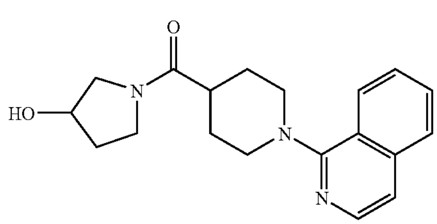 |

TABLE 1-continued

| Compound | Structure |
|---|---|
| 85 | 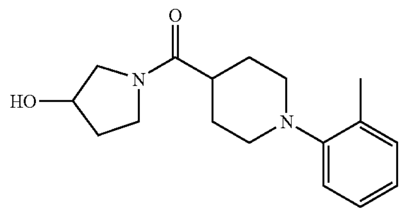 |
| 86 | 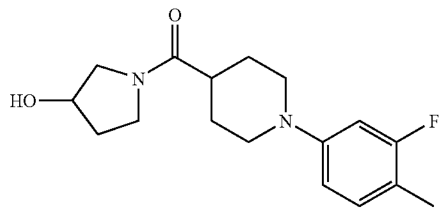 |
| 87 | 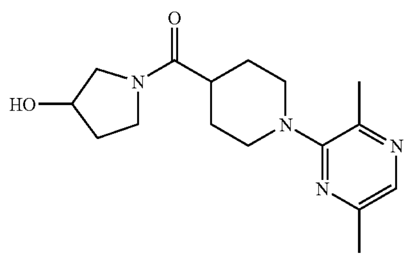 |
| 88 | 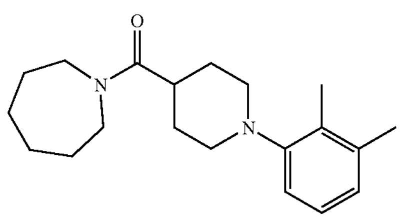 |
| 89 | 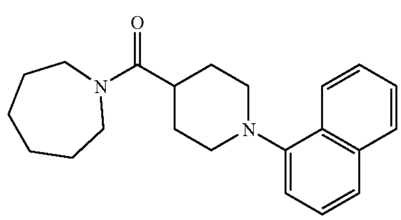 |
| 90 | 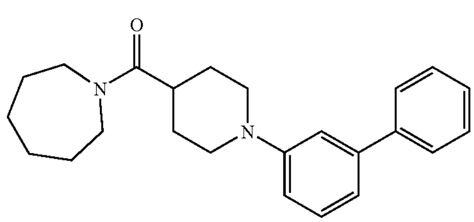 |
| 91 | 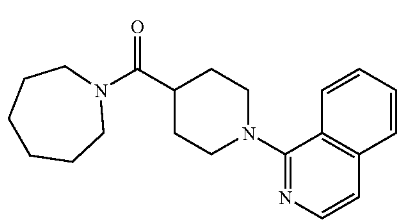 |

TABLE 1-continued
| Compound | Structure |
|---|---|
| 92 | 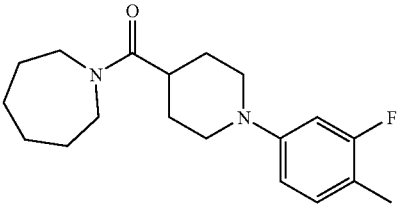 |
| 93 | 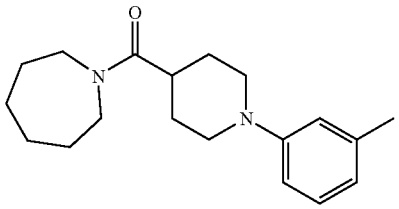 |
| 94 | 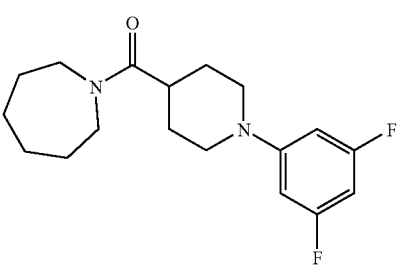 |
| 95 | 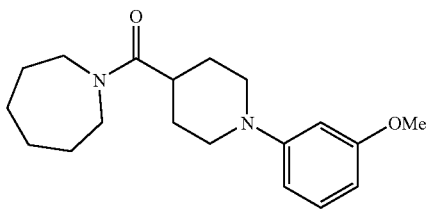 |
| 96 | 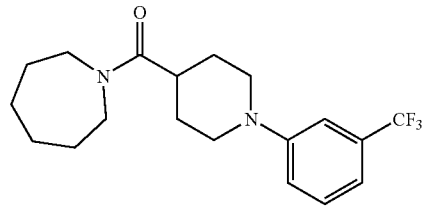 |
| 97 | 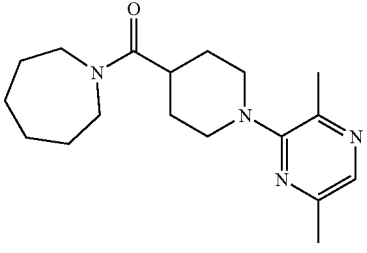 |

TABLE 1-continued
| Compound | Structure |
|---|---|
| 98 | 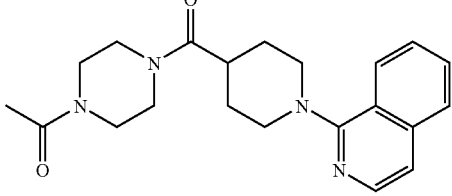 |
| 99 | 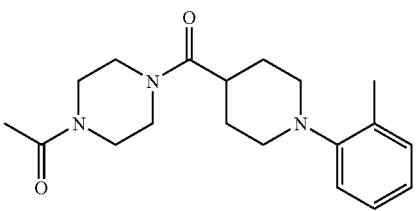 |
| 100 | 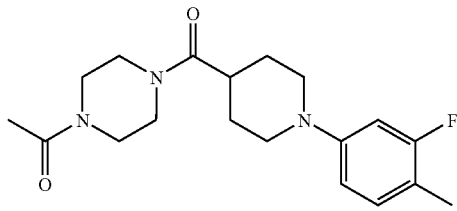 |
| 101 | 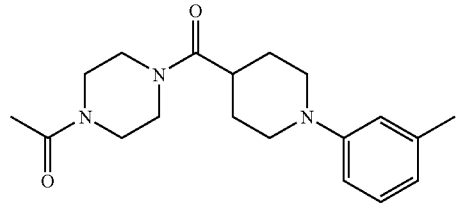 |
| 102 | 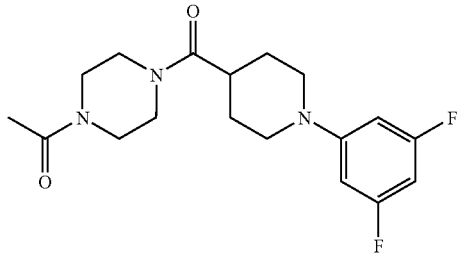 |
| 103 | 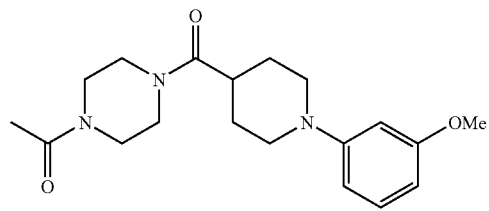 |
| 104 | 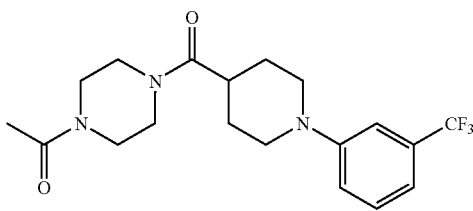 |

TABLE 1-continued

| Compound | Structure |
|---|---|
| 105 | 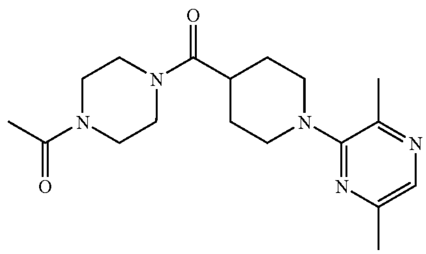 |
| 106 | 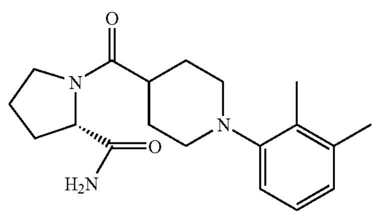 |
| 107 | 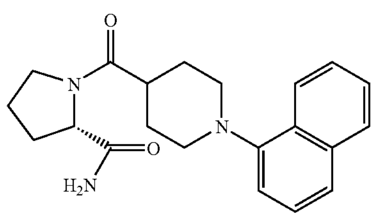 |
| 108 | 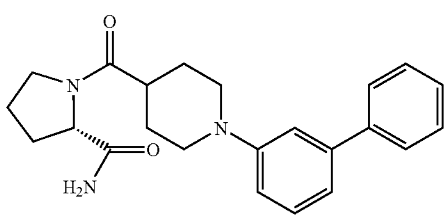 |
| 109 | 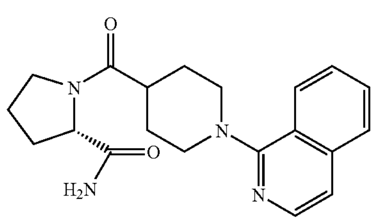 |
| 110 | 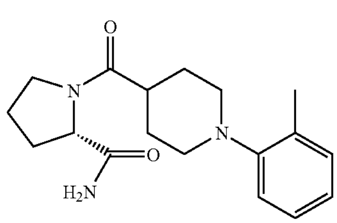 |

TABLE 1-continued

| Compound | Structure |
|---|---|
| 111 | (structure: pyrrolidine-2-carboxamide with N-acyl linked to piperidine-4-carbonyl, N-piperidine substituted with 3-fluoro-4-methylphenyl) |
| 112 | (structure: pyrrolidine-2-carboxamide with N-acyl linked to piperidine-4-carbonyl, N-piperidine substituted with 3-methylphenyl) |
| 113 | (structure: pyrrolidine-2-carboxamide with N-acyl linked to piperidine-4-carbonyl, N-piperidine substituted with 3-methoxyphenyl) |
| 114 | (structure: pyrrolidine-2-carboxamide with N-acyl linked to piperidine-4-carbonyl, N-piperidine substituted with 3-trifluoromethylphenyl) |
| 115 | (structure: pyrrolidine-2-carboxamide with N-acyl linked to piperidine-4-carbonyl, N-piperidine substituted with 3,5-difluorophenyl) |
| 116 | (structure: pyrrolidine-2-carboxamide with N-acyl linked to piperidine-4-carbonyl, N-piperidine substituted with 3,6-dimethylpyrazin-2-yl) |

TABLE 1-continued
| Compound | Structure |
|---|---|
| 117 | 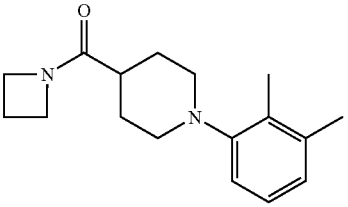 |
| 118 | 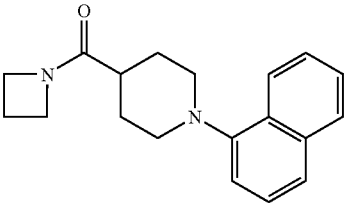 |
| 119 | 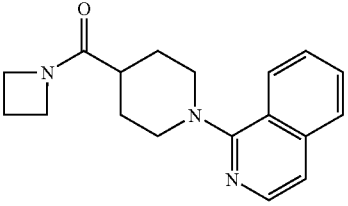 |
| 120 | 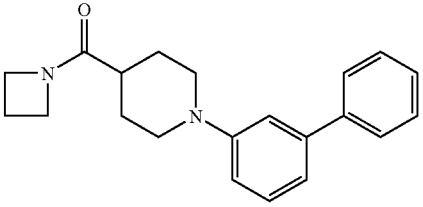 |
| 121 | 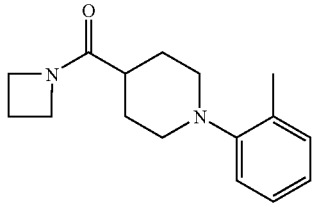 |
| 122 | 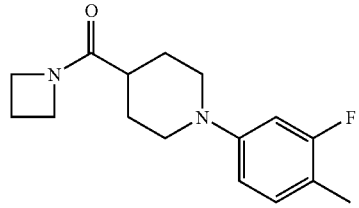 |
| 123 | 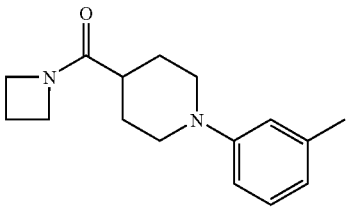 |

TABLE 1-continued
| Compound | Structure |
|---|---|
| 124 | 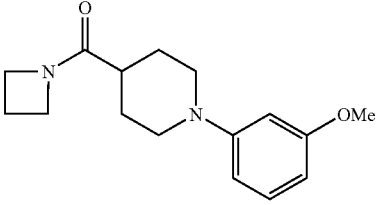 |
| 125 | 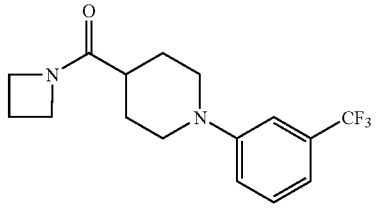 |
| 126 | 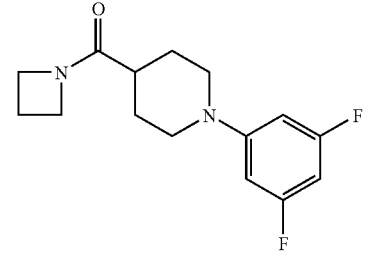 |
| 127 | 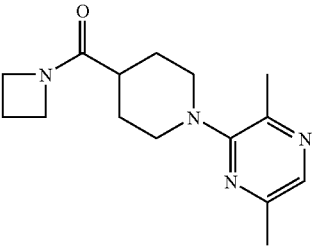 |
| 128 | 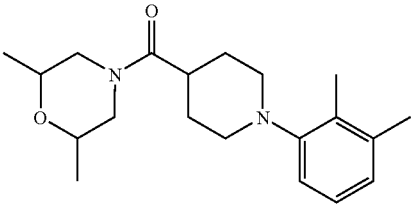 |
| 129 | 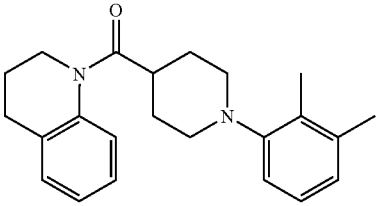 |

TABLE 1-continued

| Compound | Structure |
|---|---|
| 130 | 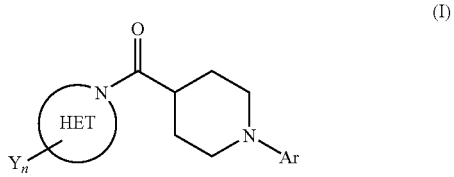 |

BIOLOGICAL EXAMPLES

The compounds of the invention were tested using a high throughput VR-1 FLIPR assay.

Human VR₁ Functional Assay

The functional activity of the test compounds was determined by measuring changes in intracellular calcium concentration using a $Ca^{++}$-sensitive fluorescent dye and FLIPR™ technology. Increases in $Ca^{++}$ concentration were readily detected upon challenge with resiniferatoxin (RTX). A431 cells expressing human VR1 were seeded on polystyrene 384-well back walled clear bottom assay plates coated with collagen and incubated for 3-4 hours at 37° C. with 5% $CO_2$ in DMEM. Plates were loaded with 15 μL of 2× Dye Solution, incubated for 1-1.5 hours and subsequently tested for agonist-induced increases in intracellular $Ca^{2+}$ levels using FLIPR™ technology. Cells were challenged with test compounds (at varying concentrations) and intracellular $Ca^{++}$ was measured prior to the addition of resiniferatoxin to all wells to elicit ~80% maximal response. $EC_{50}$ or $IC_{50}$ values were determined from dose-response studies.

The compounds of the invention were found to be potent modulators of VR1, and in particular, $EC_{50}$ values were measured as tabulated in Table 2, below.

TABLE 2

| Compound | $EC_{50}$ (μM) |
|---|---|
| 1 | 0.23 |
| 2 | 0.24 |
| 3 | 0.27 |
| 4 | 0.27 |
| 5 | 0.33 |
| 6 | 0.34 |
| 7 | 0.76 |
| 8 | 0.91 |
| 9 | 1.04 |
| 10 | 1.3 |
| 11 | 1.42 |
| 12 | 1.50 |
| 13 | 1.59 |
| 14 | 1.64 |
| 15 | 1.85 |
| 16 | 1.89 |
| 17 | 1.91 |
| 18 | 1.97 |
| 19 | 2.00 |
| 20 | 2.05 |
| 21 | 2.20 |
| 22 | 2.30 |
| 23 | 2.80 |
| 24 | 3.10 |
| 25 | 3.20 |
| 26 | 3.26 |

TABLE 2-continued

| Compound | $EC_{50}$ (μM) |
|---|---|
| 27 | 3.53 |
| 28 | 3.70 |
| 29 | 3.80 |
| 30 | 3.80 |
| 31 | 4.00 |
| 32 | 4.10 |
| 33 | 4.10 |
| 34 | 4.37 |
| 35 | 4.60 |
| 36 | 5.20 |
| 37 | 5.40 |
| 38 | 7.84 |

The invention claimed is:

1. A compound of formula (I)

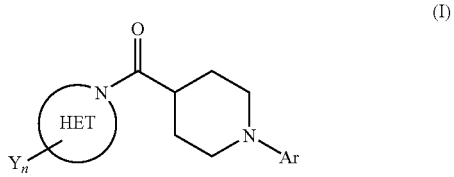

wherein

is thiomorpholin-4-yl;
Y is bonded to

at a substitutable atom and is independently selected from the group consisting of hydrogen; hydroxyl; $R^1$; $R^1O$—; $R^1S$—; $CF_3O$—; $R^1S(O)$—; $R^1SO_2$—; —LCOX; $C_{6-10}$aryl;

n is an integer from 0 to 4;

Ar is phenyl; naphthyl; a 5-6 membered heteroaryl ring selected from the group consisting of furan, imidazole, isothiazole, isoxazole, oxadiazole, oxazole, pyran, pyrazine, pyrazole, pyridazine, pyrrole, tetrazole, thiadiazole, triazine, and triazole; or a fused 5,6 or 6,6 heteroaryl selected from the group consisting of benzimidazole, benzisoxazole, benzofiaran, benzoxazole, benzthiazole, benzothiophene, cinnoline, indazole, indole, indoline, indolizine, isobenzofiaran, isoindole, isoindoline, isoquinoline, naphthyridine, pthalazine, pteridine, pyrrolizine, quinoline, and quinolizine;

$R^1$ is $C_{1-10}$alkyl;

L is —NH—, a direct bond, —O—, or —CH$_2$—;

X is H, $R^1$, HO, $R^1$O—, $R^1$S—, —NH$_2$, $R^1$NH—, or $(R^1)_2$N—; and enantiomers, diastereomers, tautomers, solvates, and pharmaceutically acceptable salts thereof.

2. A compound according to claim 1 wherein Y is OH.

3. A compound according to claim 1 wherein Y is methylcarbonyl.

4. A compound according to claim 1 wherein Y is methyl.

5. A compound according to claim 1 wherein n is 0.

6. A compound according to claim 1 wherein n is 1.

7. A compound according to claim 1 wherein Ar is phenyl.

8. A compound according to claim 1 wherein Ar is naphthyl.

9. A compound according to claim 1 wherein Ar is substituted with 1-2 substituents independently selected from the group consisting of halogen, $R^1$, $R^1$O—, fluorinated $C_{1-10}$alkyl, phenyl, and fluorinated $C_{1-10}$alkyl.

10. A compound according to claim 1 wherein Ar is substituted with 1-2 substituents independently selected from the group consisting of methyl, phenyl, CF$_3$—, F, and CH$_3$O—.

11. A compound according to claim 1 wherein Ar is phenyl optionally substituted with 1-2 substituents independently selected from the group consisting of halogen, $R^1$, $R^1$O—, fluorinated $C_{1-10}$alkyl, phenyl, and fluorinated $C_{1-10}$alkyl.

12. A compound according to claim 1 wherein n is 1 and Y is OH or methylcarbonyl.

13. A compound according to claim 1 wherein Ar is biphenyl, methylphenyl or dimethylphenyl.

14. A compound selected from the group consisting of:

Thiomorpholin-4-yl-(1-o-tolyl-piperidin-4-yl)-methanone;

[1-(3-Fluoro-4-methyl-phenyl)-piperidin-4-yl]-thiomorpholin-4-yl-methanone;

[1-(3,4-Dimethyl-phenyl)-piperidin-4-yl]-thiomorpholin-4-yl-methanone;

[1-(2,3-Dimethyl-phenyl)-piperidin-4-yl]-thiomorpholin-4-yl-methanone;

[1-(3,5-Difluoro-phenyl)-piperidin-4-yl]-thiomorpholin-4-yl-methanone;

(1-Biphenyl-3-yl-piperidin-4-yl)-thiomorpholin-4-yl-methanone;

[1-(3-Methoxy-phenyl)-piperidin-4-yl]-thiomorpholin-4-yl-methanone;

(1-Naphthalen-1-yl-piperidin-4-yl)-thiomorpholin-4-yl-methanone;

(1-Isoquinolin-1-yl-piperidin-4-yl)-thiomorpholin-4-yl-methanone;

Thiomorpholin-4-yl-( 1-m-tolyl-piperidin-4-yl)-methanone;

Thiomorpholin-4-yl-[1-(3-trifluoromethyl-phenyl)-piperidin-4-yl]-methanone;

[1-(3,6-Dimethyl-pyrazin-2-yl)-piperidin-4-yl]-thiomorpholin-4-yl-methanone.

\* \* \* \* \*

UNITED STATES PATENT AND TRADEMARK OFFICE
CERTIFICATE OF CORRECTION

PATENT NO. : 7,622,579 B2
APPLICATION NO. : 11/168213
DATED : November 24, 2009
INVENTOR(S) : Gaul et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 995 days.

Signed and Sealed this

Fourteenth Day of December, 2010

David J. Kappos
*Director of the United States Patent and Trademark Office*